US009788776B1

(12) United States Patent
Thompson et al.

(10) Patent No.: US 9,788,776 B1
(45) Date of Patent: Oct. 17, 2017

(54) PROTEIN M-BASED IN VIVO DIAGNOSTIC SYSTEM AND DETECTION METHOD

(71) Applicant: Verily Life Sciences LLC, Mountain View, CA (US)

(72) Inventors: Jason Donald Thompson, Palo Alto, CA (US); Jerrod Joseph Schwartz, San Francisco, CA (US); Joshua Simon Klein, Mountain View, CA (US)

(73) Assignee: Verily Life Sciences LLC, Mountain View, CA (US)

(*) Notice: Subject to any disclaimer, the term of this patent is extended or adjusted under 35 U.S.C. 154(b) by 363 days.

(21) Appl. No.: 14/492,391

(22) Filed: Sep. 22, 2014

(51) Int. Cl.

| | |
|---|---|
| ***A61B 5/1455*** | (2006.01) |
| ***A61B 5/154*** | (2006.01) |
| ***G01N 33/543*** | (2006.01) |
| ***A61B 5/00*** | (2006.01) |

(52) U.S. Cl.
CPC .......... *A61B 5/1545* (2013.01); *A61B 5/0071* (2013.01); *A61B 5/681* (2013.01); *G01N 33/54346* (2013.01)

(58) Field of Classification Search
CPC ..... A61B 5/1455; A61B 5/681; A61B 5/0071; G01N 33/54346
See application file for complete search history.

(56) References Cited

U.S. PATENT DOCUMENTS

| | | | |
|---|---|---|---|
| 4,640,898 | A | 2/1987 | Halfman |
| 7,906,280 | B2 | 3/2011 | Bruno et al. |
| 8,153,390 | B2 | 4/2012 | Bradshaw et al. |
| 8,574,925 | B2 | 11/2013 | Jibu |
| 8,715,951 | B2 | 5/2014 | Parhami-Seren et al. |
| 2005/0118619 | A1 | 6/2005 | Xia et al. |
| 2009/0186342 | A1 | 7/2009 | Bruno et al. |
| 2012/0094277 | A1 | 4/2012 | Bruno et al. |
| 2012/0219961 | A1 | 8/2012 | Bruno et al. |
| 2014/0005069 | A1 | 1/2014 | Yang et al. |
| 2014/0025000 | A1 | 1/2014 | Currie et al. |

FOREIGN PATENT DOCUMENTS

| | | | |
|---|---|---|---|
| WO | 2006107921 | A2 | 10/2006 |
| WO | 2009105583 | A1 | 8/2009 |
| WO | 2014014897 | A2 | 1/2014 |

OTHER PUBLICATIONS

Arruebo, et al., "Antibody-Conjugated Nanoparticles for Biomedical Applications", Journal of Nanomaterials, 2009, vol. 2009, Article ID 439389, 24 pages (available at http://dx.doi.org/10.1155/2009/439389).

Auld, et al., "Receptor Binding Assays for HTS and Drug Discovery", Assay Guidance Manual, May 1, 2012, pp. 1-33 (available at http://www.ncbi.nlm.nih.gov/books/NBK91992/).

Davenport, et al., "Radioligand Binding Assays: Theory and Practice", Current Directions in Radiopharmaceutical Research and Development, 1996, vol. 30, pp. 169-179.

Grover, et al., "A Structurally Distinct Human Mycoplasma Protein that Generically Blocks Antigen-Antibody Union", Science, Feb. 7, 2014, vol. 343, pp. 656-661.

Held, "An Introduction to Fluorescence Resonance Energy Transfer (FRET) Technology and its Application in Bioscience", Jun. 20, 2005, pp. 1-10, from BioTek Catalog (available at http://www.biotek.com/resources/articles/fluorescence-resonance-energy-transfer.html).

Marras, "Selection of Fluorophore and Quencher Pairs for Fluorescent Nucleic Acid Hybridization Probes", Methods in Molecular Biology, 2006, vol. 335, pp. 3-16.

"Antibody", Wikipedia, pp. 1-22. [Retrieved from the Internet Sep. 8, 2014:<URL:http://en.wikipedia.org/wiki/Antibody>].

"Fluorescent Glucose Biosensor", Wikipedia, pp. 1-16. [Retrieved from the Internet Sep. 10, 2014:<URL:http://en.wikipedia.org/wiki/Fluorescent_glucose_biosensor>].

"Fluorescent Labelling", Wikipedia, pp. 1-2. [Retrieved from the Internet Sep. 8, 2014:<URL:http://en.wikipedia.org/wiki/Fluorescent_labelling>].

"Forster Resonance Energy Transfer", Wikipedia, pp. 1-11. [Retrieved from the Internet Jul. 29, 2014:<URL:http://en.wikipedia.org/wiki/Forster_resonance_energy_transfer>].

"Real-Time PCR: Guidelines for Use of Fluorophores and Quenchers", Technical Bulletin 002-2011, Microsynth AG, pp. 1-2. (Abstract only).

*Primary Examiner* — Michael G Hartley
*Assistant Examiner* — Robert Cabral
(74) *Attorney, Agent, or Firm* — McDonnell Boehnen Hulbert & Berghoff LLP

(57) ABSTRACT

A wearable device mounted on a living body can detect an analyte response signal transmitted from tissue in the living body. The tissue contains at particles conjugated to at least one complex of (i) an antibody labeled with a fluorophore, the labeled antibody having a target analyte binding site; and (ii) protein M labeled with a quencher that is complimentary to the fluorophore of the labeled antibody, wherein the labeled protein M competes with the target analytes for the target analyte binding site on the labeled antibody; wherein the fluorophore and quencher are spectrally matched such that there is a detectable change in the fluorescent signal. The analyte response signal is related to interaction of the target analytes with the complexes. A processor can determine a presence or absence of the analytes based on the analyte response signal.

10 Claims, 24 Drawing Sheets

PROTEIN M-BASED IN VIVO DIAGNOSTIC SYSTEM AND DETECTION METHOD

BACKGROUND

Unless otherwise indicated herein, the materials described in this section are not prior art to the claims in this application and are not admitted to be prior art by inclusion in this section.

A number of diagnostic methods have been developed to evaluate physiological conditions of a person by detecting and/or measuring one or more analytes in a person's blood or other bodily fluids or tissues. The one or more target analytes could be any analytes that, when present in or absent from the blood, or present at a particular concentration or range of concentrations, may be indicative of a medical condition or health state of the person. The one or more target analytes could include enzymes, reagents, hormones, proteins, cells or other molecules, such as carbohydrates, e.g., glucose.

Interest in measuring the binding interactions between antibodies and their specific antigens has resulted in the application of a broad array of technologies to the development of immunodiagnostics. Because of its high sensitivity, fluorescence-based diagnostic assays based on Forster Resonance Energy transfer (FRET) have received considerable attention and have been broadly applied in biology and chemistry to obtain information about proteins and other biological molecules. Such assays are divided into two categories: homogeneous and heterogeneous, the latter involving physical separation of the assay mixture before detection while the former requires no separation steps. Most fluoroimmunoassays are heterogeneous and are often competitive assays in which a fluorescent labeled antigen (or antibody) completes for binding with an unlabeled antigen (or antibody). In such assays, the fluorescent labeled species are referred to as the tracer, and the unlabeled species are the analyte. Depending on the assay being performed, the analyte can be either an antigen or an antibody. After removal of unbound analyte and tracer, the signal intensity from the bound tracer is inversely proportional to the analyte concentration in the original solution.

SUMMARY

Some embodiments of the present disclosure provide a composition including: at least one particle conjugated to at least one complex, the complex including (i) an antibody labeled with a fluorophore, the labeled antibody having a target analyte binding site; and (ii) a protein M labeled with a quencher that is complimentary to the fluorophore of the labeled antibody and bound to the target analyte binding site, wherein the labeled protein M competes with a target analyte for a target analyte binding site on the labeled antibody; wherein the fluorophore and quencher are spectrally matched such that there is a detectable change in the fluorescent signal of the labeled antibody when the fluorophore and the quencher are moved into or out of functional proximity, and wherein fluorescent light level changes proportionately in response to the amount of target analytes that are able to bind with the labeled antibody.

Another embodiment of the present disclosure provide a method which includes: (a) contacting a solution with at least one nanoparticle conjugated to at least one complex, the complex including (i) an antibody labeled with a fluorophore, the labeled antibody having a target analyte binding site; and (ii) protein M labeled with a quencher that is complimentary to the fluorophore of the labeled antibody and bound to the target analyte binding site, wherein the labeled protein M competes with the target analyte for the target analyte binding site on the labeled antibody; wherein the fluorophore and quencher are spectrally matched such that there is a detectable change in the fluorescent signal of the labeled antibody when the fluorophore and the quencher are moved into or out of functional proximity, and wherein fluorescent light levels change proportionately in response to the amount of target analytes in solution that are able to bind with the labeled antibody; and (b) measuring the fluorescence light level related to a presence of the target analytes in the solution.

Another embodiment of the present disclosure provides a system which includes: a wearable device including: (i) a mount configured to mount the wearable device on an external surface of a living body and (ii) a detector configured to detect an analyte response signal transmitted from tissue through the external surface, wherein the tissue contains at least one particle conjugated to at least one complex comprising (i) an antibody labeled with a fluorophore, the labeled antibody having a target analyte binding site; and (ii) protein M labeled with a quencher that is complimentary to the fluorophore of the labeled antibody and bound to the target analyte binding site of the labeled antibody; wherein the labeled protein M competes with target analytes for the target analyte binding site on the labeled antibody; wherein the fluorophore and quencher are spectrally matched such that there is a detectable change in the fluorescent signal of the labeled antibody when the fluorophore and the quencher are moved into or out of functional proximity; wherein fluorescent light levels change proportionately in response to the amount of target analytes that are able to bind with the labeled antibody; wherein the at least one complex is configured to bind with one or more target analytes; wherein presence or absence of the one or more target analytes is correlated with a biological state of the living body; and wherein the analyte response signal is related to interaction of the one or more target analytes with the at least one complex; and (iii) a processor configured to determine a presence or absence of the one or more target analytes based on the analyte response signal.

Another embodiment of the present disclosure relates to a method which includes: (a) introducing at least one particle conjugated to at least one complex into the living body, the at least one complex comprising (i) an antibody labeled with a fluorophore, the labeled antibody having a target analyte binding site; and (ii) protein M labeled with a quencher that is complimentary to the fluorophore of the labeled antibody and bound to the target analyte binding site of the labeled antibody, wherein the labeled protein M competes with target analytes for the target analyte binding site on the labeled antibody; wherein the fluorophore and quencher are spectrally matched such that there is a detectable change in the fluorescent signal of the labeled antibody when the fluorophore and the quencher are moved into or out of functional proximity; wherein fluorescent light levels change proportionately in response to the amount of target analytes that are able to bind with the labeled antibody; wherein the at least one complex is configured to bind with one or more target analytes, wherein presence or absence of the one or more target analytes in the living body is correlated with the biological state of the living body; (b) detecting, by a wearable device mounted on an external surface of the living body, a signal transmitted from the living body, wherein the signal includes an analyte response signal that is related to binding of the one or more target analytes with the at least one complex; and (c) determining a presence or absence of the one or more target analytes based on the analyte response signal.

These as well as other aspects, advantages, and alternatives, will become apparent to those of ordinary skill in the art by reading the following detailed description, with reference where appropriate to the accompanying drawings.

BRIEF DESCRIPTION OF THE DRAWINGS

FIG. 10 is a functional block diagram of an example system including a wearable device and a remote device.

DETAILED DESCRIPTION

Figure 1:
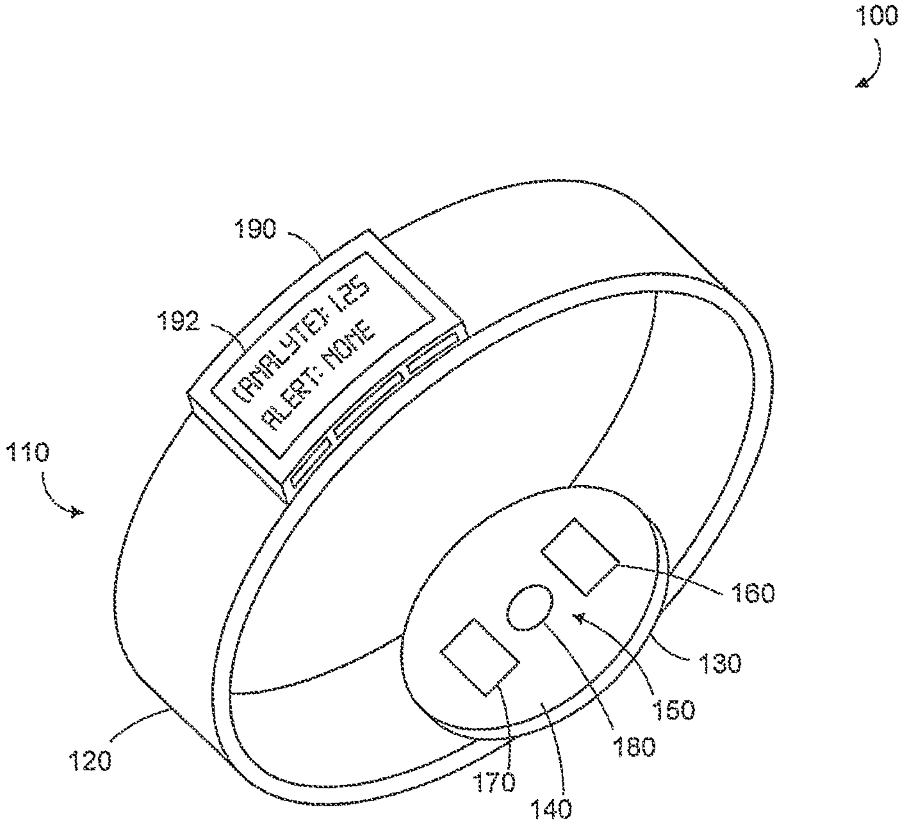
FIG. 1 is a perspective view of an example wearable device.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Further, while embodiments disclosed herein make reference to use on or in conjunction with a living human body, it is contemplated that the disclosed methods, systems and devices may be used in any environment where non-invasive detection of an analyte is desired. The environment may be any living or non-living body or a portion thereof, a fluid conduit, a fluid reservoir, etc. For example, one of skill in the art will recognize that the embodiments disclosed herein may be used to sense analytes present in a water system. Moreover, while the present disclosure describes embodiments for use in vivo, one of skill in the art will also recognize that in vitro applications are possible as well. Accordingly, the environment may also include a test tube or other vessel for holding a fluid.

I. Overview

A diagnostic system can non-invasively detect and measure a plurality of physiological parameters of a person, which can include any parameters that may relate to the person's health. For example, the system could include sensors for measuring blood pressure, pulse rate, skin temperature, etc. At least some of the physiological parameters may be obtained by the system non-invasively detecting and/or measuring one or more analytes in blood circulating in subsurface vasculature. The one or more analytes could be any analytes that, when present in or absent from the blood, or present at a particular concentration or range of concentrations, may be indicative of a medical condition or health of the person. For example, the one or more analytes could include enzymes, hormones, proteins, cells or other molecules.

In an example embodiment, the system obtains at least some of the health-related information by detecting the binding or interaction of a clinically-relevant analyte to or with materials such as particles, for example, microparticles or nanoparticles, introduced into a lumen of the subsurface vasculature that have been functionalized with a complex of an antibody having a target analyte binding site and protein M bound non-specifically to the target analyte (also referred to as a "particle conjugate" or "antibody-particle conjugate") that has a specific affinity to bind to or interact with the specific analyte. Protein M is a newly discovered antibody-binding target derived from human mycoplasma bacteria that has an unusual property of binding to any antibody, generically blocking antibody-antigen binding unlike any known protein. Specifically, protein M binds to a small conserved region, called the complementary site, of an antibody's antigen binding arm and then extends a portion of itself over the antibody's main antigen binding site. Further, it has been discovered that protein M can be readily displaced by a target analyte specific to the target analyte binding site of the antibody and thus serve a useful role as a generic antigen for FRET-based competitive assays. The term "binding" is understood in its broadest sense to also include a detectable interaction between the clinically relevant analyte and the functionalized materials, e.g., functionalized particles or particle conjugates. The particle conjugates can be introduced into the person's blood stream by injection, ingestion, inhalation, transdermally, or in some other manner.

The particles can be functionalized by covalently or otherwise attaching or associating an antibody that specifically binds or otherwise interacts with a particular clinically-relevant analyte with a defined affinity to the target analyte. The antibody is complexed to protein M which can be displaced competitively by the target analyte specific to the antibody. Both the antibody and protein M are labeled with a fluorophore-quencher pair that are complementary to each. Other compounds or molecules, such as fluorophores or autofluorescent or luminescent markers or non-optical contrast agents (e.g. acoustic impedance contrast, RF contrast and the like), which may assist in interrogating the particles in vivo, may also be attached to the particles.

The particles can have a diameter that is less than about 20 micrometers. In some embodiments, the particles have a diameter on the order of about 10 nanometers to 1 micrometer. In further embodiments, small particles on the order of 10-100 nanometers in diameter may be assembled to form a larger "clusters" or "assemblies on the order of 1-10 micrometers. Those of skill in the art will understand a "particle" in its broadest sense and that it may take the form of any fabricated material, a molecule, tryptophan, a virus, a phage, etc. Further, a particle may be of any shape, for example, spheres, rods, non-symmetrical shapes, etc.

In some examples, the particles may also be magnetic and can be formed from a paramagnetic, super-paramagnetic or ferromagnetic material or any other material that responds to a magnetic field. Alternatively, the particles may also be made of non-magnetic materials such as polystyrene. Where magnetic particles are used, the system may include a magnet that can direct into the portion of subsurface vasculature a magnetic field that is sufficient to manipulate antibody-magnetic particle conjugates in a lumen of that portion of subsurface vasculature, for example, to collect or slow down in a certain area. However, measurements may be taken without localized "collection" of the antibody-particle conjugates. The system may be configured to activate the magnetic field periodically, such as at certain times of the day (e.g., every hour).

The system may further include one or more data collection systems for interrogating, in a non-invasive manner, the antibody-particle conjugates present in a lumen of the subsurface vasculature in a particular local area. In one example, the system includes a detector configured to detect a response signal transmitted from a portion of subsurface vasculature. The response signal can include both an analyte response signal, which can be related to the interaction of the one or more target analytes with the antibody-particle conjugates, and a background noise signal. For example, the antibody-particle conjugates include a fluorescent marker or label on the antibody configured to produce a response signal in the form of fluorescence radiation produced in response to a FRET reaction initiated, at least in part, to the binding of the target analyte to the particle and the displacement of the labeled protein M from the target binding site.

In one embodiment, the system includes an interrogating signal source for transmitting an interrogating signal that can penetrate into a portion of subsurface vasculature, or another body system, and a detector for detecting a response signal that is transmitted from the portion of subsurface vasculature, or other body system, in response to the interrogating signal. The interrogating signal can be any kind of signal that is benign to the patient, such as an optical signal and results in a response signal that can be used to measure a physiological parameter or, more particularly, that can detect the binding or interaction of the clinically-relevant analyte to the antibody-particle conjugates. In one example, where the antibody-particle conjugates include a fluorophore, the interrogating signal is an optical signal with a wavelength that can excite the fluorophore and penetrate the skin or other tissue and subsurface vasculature (e.g., a wavelength in the range of about 500 to about 1000 nanometers), and the response signal is fluorescence radiation from the fluorophore that can penetrate the subsurface vasculature and tissue to reach the detector.

Additionally, the system may further include a modulation source configured to modulate the analyte response signal. The modulation source can be configured to modulate the analyte response signal differently than the background noise signal. To this end, the modulation may help to discern between the target analyte and, essentially, everything else in the body by, for example, increasing the signal-to-noise ratio. Generally, the modulation may include any spatial, temporal, spectral, thermal, magnetic, mechanical, electrical, acoustic, chemical, or electrochemical, etc. modulation technique or any combination thereof.

In some scenarios, it may also be useful to detect and distinguish both the analyte response signal-related to antibody-particle conjugates bound to or interacting with target analyte(s)—and an "unbound" particle signal—related to antibody-particle conjugates not bound to or interacting with target analyte(s). For example, in some measurement or characterization schemes, it may be useful to determine the percentage of antibody-particle conjugates introduced into the body that have bound to the target analyte. In such cases, the modulation source may be configured to modulate the analyte response signal differently than the unbound particle signal.

Data collected by the detector may be sent to a processor for analysis. The processor may be configured to non-invasively detect the one or more target analytes by differentiating the analyte response signal from the background noise signal based, at least in part, on the modulation. In some cases, the processor may further be configured to differentiate the analyte response signal from the unbound particle signal. Further, the processor may be configured to determine the concentration of a particular target analyte in the blood from, at least in part, the analyte response signal. The detection and concentration data processed by the processor may be communicated to the patient, transmitted to medical or clinical personnel, locally stored or transmitted to a remote server, the cloud, and/or any other system where the data may be stored or accessed at a later time.

The processor may be located on an external reader, which may be provided as an external body-mounted device, such as a necklace, wristwatch, eyeglasses, a mobile phone, a handheld or personal computing device or some combination thereof. Data collected by the detector may be transmitted to the external reader via a communication interface. Control electronics can wirelessly communicate the data to the external reader by modifying the impedance of an antenna in communication with the detector so as to characteristically modify the backscatter from the antenna. In some examples, the external reader can operate to intermittently interrogate the detector to provide a reading by radiating sufficient radiation to power the detector to obtain a measurement and communicate the result. In this way, the external reader can acquire a series of analyte identification and concentration measurements over time without continuously powering the detector and/or processor. The processor may also be provided at another location distal to the detector, and the detector data is communicated to the processor via a wired connection, a memory card, a USB device or other known method. Alternatively, the processor may be located proximal to the detector and may be configured to locally analyze the data that it collects and then transmit the results of the analysis to an external reader or server.

The external reader may include a user interface, or may further transmit the collected data to a device with a user interface that can indicate the results of the data analysis. In this way, the person wearing, holding or viewing the device can be made aware of the analysis and/or potential medical conditions. The external reader may also be configured to produce an auditory or tactile (vibration) response to alert the patient of a medical condition. Further, the external reader may also be configured to receive information from the patient regarding his/her health state, wellness state, activity state, nutrition intake and the like, as additional input information to the processor. For example, the user may input a health or wellness state, such as, experiencing migraine symptoms, jittery, racing heart, upset stomach, feeling tired, activity state including types and duration of physical activity nutrition intake including meal timing and composition, and other parameters including body weight, medication intake, quality of sleep, stress level, personal care products used, environmental conditions, social activity, etc. Further, the reader may also receive signals from one or more other detectors, such as a pedometer, heart rate sensor, blood pressure sensor, blood oxygen saturation level, body temperature, GPS or other location or positioning sensors, microphone, light sensor, etc.

The system may be configured to obtain data during pre-set measurement periods or in response to a prompt. For example, the system may be configured to operate the detector and collect data once an hour. In other examples, the system may be configured to operate the detector in response to a prompt, such as a manual input by the patient or a physician. The system may also be configured to obtain data in response to an internal or external event or combination of events, such as during or after physical activity, at rest, at high pulse rates, high or low blood pressures, cold or hot weather conditions, etc. In other examples, the system could operate the detector more frequently or less frequently, or the system could measure some analytes more frequently than others.

Data collected by the system may be used to notify the patient of, as described above, analyte levels or of an existing or imminent medical emergency. In some examples, the data may be used to develop an individual baseline profile for the patient. The baseline profile may include patterns for how one or more of the patient's analyte levels typically change over time, such as during the course of a day, a week, or a month, or in response to consumption of a particular type of food/drug. The baseline profile, in essence, may establish "normal" levels of the measured analytes for the patient. Additional data, collected over additional measurement periods, may be compared to the baseline profile. If the additional data is consistent with the patterns embodied in the baseline profile, it may be determined that the patient's condition has not changed. On the other hand, if the additional data deviates from the patterns embodied in the baseline profile, it may be determined that the patient's condition has changed. The change in condition could, for example, indicate that the patient has developed a disease, disorder, or other adverse medical condition or may be at risk for a severe medical condition in the near future. Further, the change in condition could further indicate a change in the patient's eating habits, either positively or negatively, which could be of interest to medical personnel. Further, the patient's baseline and deviations from the baseline can be compared to baseline and deviation data collected from a population of wearers of the devices.

When a change in condition is detected, a clinical protocol may be consulted to generate one or more recommendations that are appropriate for the patient's change in condition. For example, it may be recommended that the patient inject himself/herself with insulin, change his/her diet, take a particular medication or supplement, schedule an appointment with a medical professional, get a specific medical test, go to the hospital to seek immediate medical attention, abstain from certain activities, etc. The clinical protocol may be developed based, at least in part, on correlations between analyte concentration and health state derived by the server, any known health information or medical history of the patient, and/or on recognized standards of care in the medical field. The one or more recommendations may then be transmitted to the external reader for communication to the user via the user interface.

Correlations may be derived between the analyte concentration(s) measured by the system and the health state reported by the patient. For example, analysis of the analyte data and the health state data may reveal that the patient has experienced certain adverse health conditions, such as a migraine or a heart attack, when an analyte reaches a certain concentration. This correlation data may be used to generate recommendations for the patient, or to develop a clinical protocol. Blood analysis may be complemented with other physiological measurements such as blood pressure, heart rate, body temperature etc., in order to add to or enhance these correlations.

Further, data collected from a plurality of patients, including both the analyte measurements and the indications of health state, may be used to develop one or more clinical protocols used by the server to generate recommendations and/or used by medical professionals to provide medical care and advice to their patients. This data may further be used to recognize correlations between blood analytes and health conditions among the population. Health professionals may further use this data to diagnose and prevent illness and disease, prevent serious clinical events in the population, and to update clinical protocols, courses of treatment, and the standard of care.

The above described system may be implemented as a wearable device. The term "wearable device," as used in this disclosure, refers to any device that is capable of being worn at, on or in proximity to a body surface, such as a wrist, ankle, waist, chest, ear, eye or other body part. In order to take in vivo measurements in a non-invasive manner from outside of the body, the wearable device may be positioned on a portion of the body where subsurface vasculature is easily observable, the qualification of which will depend on the type of detection system used. The device may be placed in close proximity to the skin or tissue, but need not be touching or in intimate contact therewith. A mount, such as a belt, wristband, ankle band, headband, etc. can be provided to mount the device at, on or in proximity to the body surface. The mount may prevent the wearable device from moving relative to the body to reduce measurement error and noise. Further, the mount may be an adhesive substrate for adhering the wearable device to the body of a wearer. The detector, modulation source, interrogation signal source (if applicable) and, in some examples, the processor, may be provided on the wearable device. In other embodiments, the above described system may be implemented as a stationary measurement device to which a user must be brought into contact or proximity with or as a device that may be temporarily placed or held against a body surface during one or more measurement periods.

It should be understood that the above embodiments, and other embodiments described herein, are provided for explanatory purposes, and are not intended to be limiting.

Further, the term "medical condition" as used herein should be understood broadly to include any disease, illness, disorder, injury, condition or impairment—e.g., physiologic, psychological, cardiac, vascular, orthopedic, visual, speech, or hearing—or any situation requiring medical attention.

II. Example Wearable Devices

A wearable device 100 can automatically measure one or more physiological parameters of a person wearing the device. The term "wearable device," as used in this disclosure, refers to any device that is capable of being worn at, on or in proximity to a body surface, such as a wrist, ankle, waist, chest, or other body part. In order to take in vivo measurements in a non-invasive manner from outside of the body, the wearable device may be positioned on a portion of the body where subsurface vasculature is easily observable, the qualification of which will depend on the type of detection system used. The device may be placed in close proximity to the skin or tissue, but need not be touching or in intimate contact therewith. A mount 110, such as a belt, wristband, ankle band, etc. can be provided to mount the device at, on or in proximity to the body surface. The mount 110 may prevent the wearable device from moving relative to the body to reduce measurement error and noise. In one example, shown in FIG. 1, the mount 110, may take the form of a strap or band 120 that can be worn around a part of the body. Further, the mount 110 may be an adhesive substrate for adhering the wearable device 100 to the body of a wearer.

A measurement platform 130 is disposed on the mount 110 such that it can be positioned on the body where subsurface vasculature is easily observable. An inner face 140 of the measurement platform is intended to be mounted facing to the body surface. The measurement platform 130 may house a data collection system 150, which may include at least one detector 160 for detecting at least one physiological parameter. The at least one physiological parameter could be any parameter that may relate to the health of the person wearing the wearable device. For example, the detector 160 could be configured to measure blood pressure, pulse rate, respiration rate, skin temperature, etc. At least one of the detectors 160 is configured to non-invasively measure one or more analytes in blood circulating in subsurface vasculature proximate to the wearable device. In a non-exhaustive list, detector 160 may include any one of an optical (e.g., CMOS, CCD, photodiode), acoustic (e.g., piezoelectric, piezoceramic), electrochemical (voltage, impedance), thermal, mechanical (e.g., pressure, strain), magnetic, or electromagnetic (e.g., magnetic resonance) sensor. The components of the data collection system 150 may be miniaturized so that the wearable device may be worn on the body without significantly interfering with the wearer's usual activities.

In some examples, the data collection system 150 further includes a signal source 170 for transmitting an interrogating signal that can penetrate the wearer's skin into the portion of subsurface vasculature, for example, into a lumen of the subsurface vasculature. The interrogating signal can be any kind of signal that is benign to the wearer, such as electromagnetic, magnetic, optic, acoustic, thermal, mechanical, and results in a response signal that can be used to measure a physiological parameter or, more particularly, that can detect the binding of the clinically-relevant analyte to the antibody-particle conjugates. In one example, the antibody-particle conjugates include a fluorophore. The interrogating signal may therefore be an electromagnetic radiation signal with a wavelength that can excite the fluorophore and penetrate the skin or other tissue and subsurface vasculature (e.g., a wavelength in the range of about 500 to about 1000 nanometers), and the response signal is fluorescence radiation from the fluorophore that can penetrate the subsurface vasculature and tissue to reach the detector.

In some cases, an interrogating signal is not necessary to measure one or more of the physiological parameters and, therefore, the wearable device 100 may not include a signal source 170. For example, the antibody-particle conjugates include an autofluorescent or luminescent marker, such as a photolumeniscent probe or fluorophore, that will automatically emit a response signal indicative of the binding of the clinically-relevant analyte to the antibody-particle conjugates, without the need for an interrogating signal or other external stimulus. In some examples, the antibody-particle conjugates may include a chemiluminescent marker configured to produce a response signal in the form of luminescence radiation produced in response to a chemical reaction initiated, at least in part, to the binding of the target analyte to the particle. In other examples, a photoluminescent probe in combination with the matched quencher can be used, eliminating the need for an excitation source such the interrogating signal.

A collection magnet 180 may also be included in the data collection system 150. In such embodiments, the antibody-particle conjugates may also be made of or be functionalized with magnetic materials, such as ferromagnetic, paramagnetic, super-paramagnetic, or any other material that responds to a magnetic field. The collection magnet 180 is configured to direct a magnetic field into the portion of subsurface vasculature that is sufficient to cause antibody-magnetic particle conjugates to collect in a lumen of that portion of subsurface vasculature. The magnet may be an electromagnet that may be turned on during measurement periods and turned off when a measurement period is complete so as to allow the magnetic particles to disperse through the vasculature.

The wearable device 100 may also include a user interface 190 via which the wearer of the device may receive one or more recommendations or alerts generated either from a remote server or other remote computing device, or from a processor within the device. The alerts could be any indication that can be noticed by the person wearing the wearable device. For example, the alert could include a visual component (e.g., textual or graphical information on a display), an auditory component (e.g., an alarm sound), and/or tactile component (e.g., a vibration). Further, the user interface 190 may include a display 192 where a visual indication of the alert or recommendation may be displayed. The display 192 may further be configured to provide an indication of the measured physiological parameters, for instance, the concentrations of certain blood analytes being measured.

The wearable device may, in some cases, also include a modulation source. The signal-to-noise ratio (SNR) in an analyte detection system, such as any of those described above, may be increased by modulating the analyte response signal transmitted from the subsurface vasculature (or other body system) with respect to the background signal and, in some cases, an unbound particle response signal. Such modulation can increase the system's sensitivity and ability to discern between target analytes present in the blood or other bodily fluids, versus other analytes, particles, cells, molecules, blood components, bone and tissues, etc. This can be particularly valuable with some methods of analyte characterization, such as optical methods, or where the target analytes are rare in the blood or are of a relatively small size and with fluorescence detection techniques, which can often suffer from low resolution because other tissues, cells, and molecules in the body may have some inherent fluorescent properties, creating a high level of background noise.

The modulation source may apply a modulation, configured to modulate the response signal, to the portion of the body. Specifically, the modulation source may be configured to modulate the analyte response signal differently from a background signal. The background signal may include any signal transmitted from something other than what the system is monitoring, i.e., the target analyte(s). In some examples, the background signal may be generated by other molecules, cells, or particles in the blood or other bodily fluids; tissue, such as skin, veins, muscle, etc.; bone; or other objects present in the wearer's body. A background signal may be generated by excitation of these objects from the interrogating signal, such as by generating an autofluorescence signal, or due to some inherent property of these objects, such as, chemiluminescence, etc.

In some examples, the modulation source may be configured to modulate the analyte response signal (transmitted from bound particles) differently than the unbound particle signal (transmitted from particles that are not bound or otherwise interacting with the target analyte(s)), such that the analyte response signal may be differentiated from the unbound particle signal. Such differentiation may be used to determine the number or percentage of particles bound to or interacting with the target analyte(s), which may be used to determine a concentration of the target analyte(s) in the blood or other bodily fluid, to determine if and to what extent the particles are being cleared from the body, etc.

The modulation source may include any means for modulating the response signal. In some cases, the analyte response signal may be modulated differently than the background signal, and in other cases the analyte response signal may be modulated differently than the unbound particle signal, or both. For example, the modulation source may be configured to alter the spatial, optical magnetic, electric, acoustic, and/or physical properties of the bound particles. The modulation source may be a physical construct or it may be a signal or energy applied to the body, or a combination thereof. Accordingly, the modulation may include spatial, temporal, spectral, thermal, magnetic, optical, mechanical, electrical, acoustic, chemical, or electrochemical type of modulation or any combination thereof.

Figure 2A:
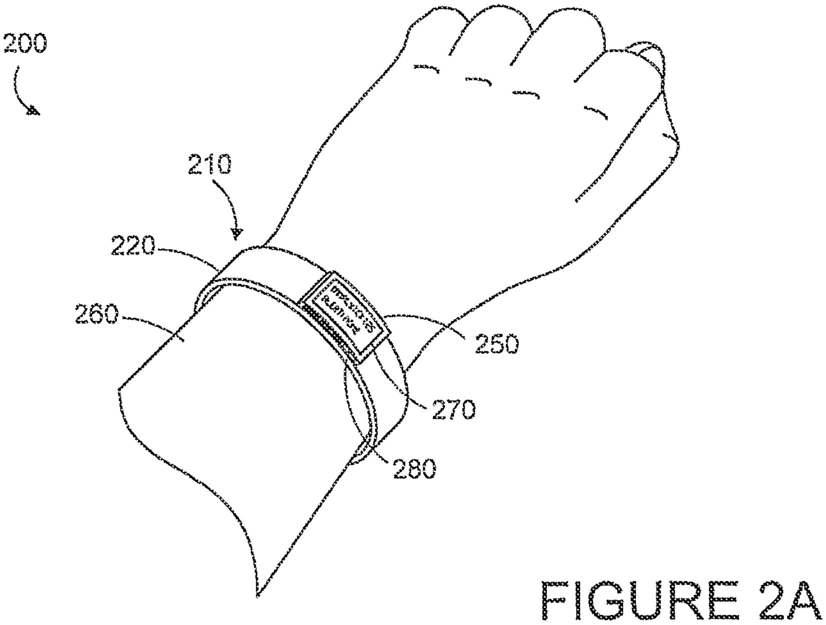
FIG. 2A is a perspective top view of an example wrist-mounted device, when mounted on a wearer's wrist.
Figure 2B:
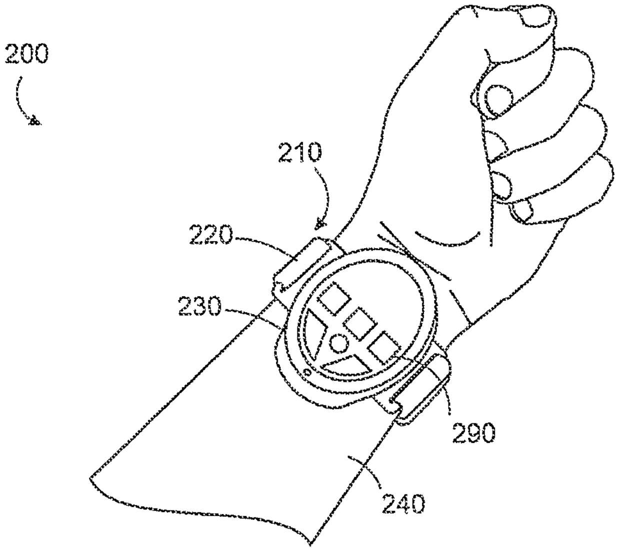
FIG. 2B is a perspective bottom view of an example wrist-mounted device shown in FIG. 2A, when mounted on a wearer's wrist.

In one example, the wearable device is provided as a wrist-mounted device, as shown in FIGS. 2A, 2B, 3A-3C, 4A, 5B and 6. The wrist-mounted device may be mounted to the wrist of a living subject with a wristband or cuff, similar to a watch or bracelet. As shown in FIGS. 2A and 2B, the wrist mounted device 200 may include a mount 210 in the form of a wristband 220, a measurement platform 230 positioned on the anterior side 240 of the wearer's wrist, and a user interface 250 positioned on the posterior side 260 of the wearer's wrist. The wearer of the device may receive, via the user interface 250, one or more recommendations or alerts generated either from a remote server or other remote computing device, or alerts from the measurement platform. Such a configuration may be perceived as natural for the wearer of the device in that it is common for the posterior side 260 of the wrist to be observed, such as the act of checking a wrist-watch. Accordingly, the wearer may easily view a display 270 on the user interface. Further, the measurement platform 230 may be located on the anterior side 240 of the wearer's wrist where the subsurface vasculature may be readily observable. However, other configurations are contemplated.

The display 270 may be configured to display a visual indication of the alert or recommendation and/or an indication of the measured physiological parameters, for instance, the concentrations of certain blood analytes being measured. Further, the user interface 250 may include one or more buttons 280 for accepting inputs from the wearer. For example, the buttons 280 may be configured to change the text or other information visible on the display 270. As shown in FIG. 2B, measurement platform 230 may also include one or more buttons 290 for accepting inputs from the wearer. The buttons 290 may be configured to accept inputs for controlling aspects of the data collection system, such as initiating a measurement period, or inputs indicating the wearer's current health state (i.e., normal, migraine, shortness of breath, heart attack, fever, "flu-like" symptoms, food poisoning, etc.).

Figure 3A:
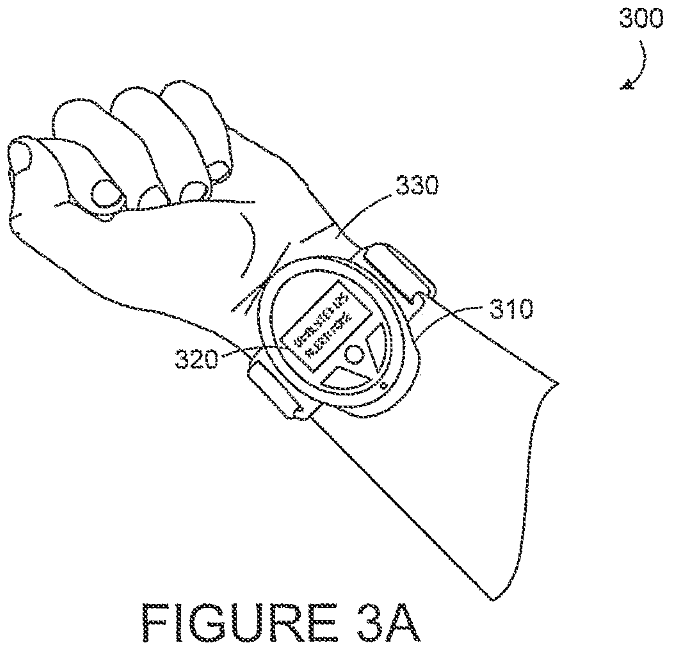
FIG. 3A is a perspective bottom view of an example wrist-mounted device, when mounted on a wearer's wrist.
Figure 3B:
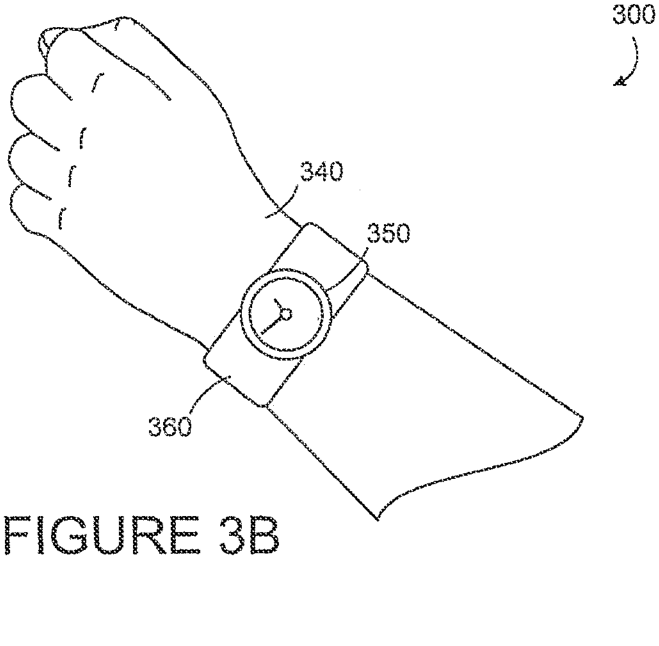
FIG. 3B is a perspective top view of an example wrist-mounted device shown in FIG. 3A, when mounted on a wearer's wrist.
Figure 3C:
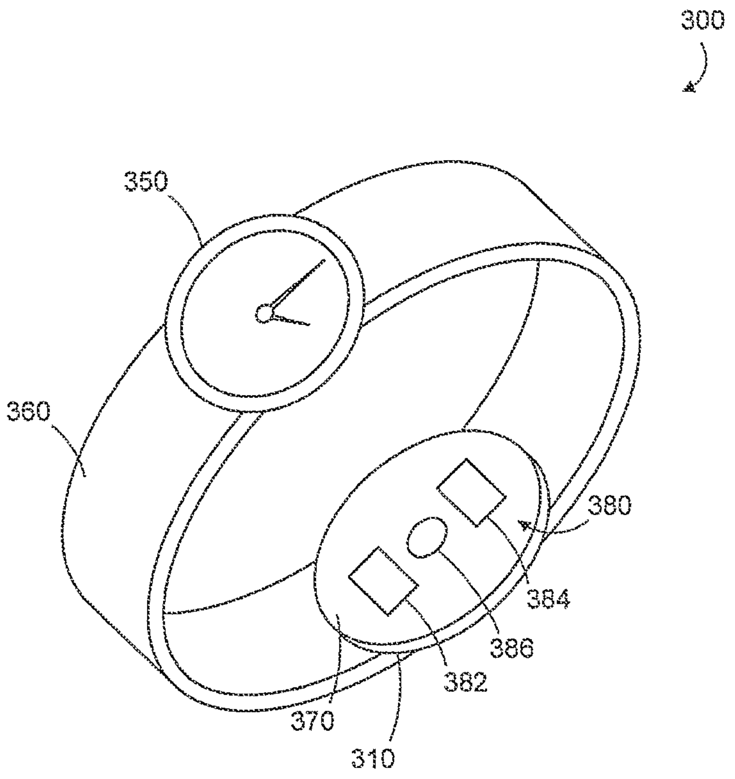
FIG. 3C is a perspective view of an example wrist-mounted device shown in FIGS. 3A and 3B.

In another example wrist-mounted device 300, shown in FIGS. 3A-3C, the measurement platform 310 and user interface 320 are both provided on the same side of the wearer's wrist, in particular, the anterior side 330 of the wrist. On the posterior side 340, a watch face 350 may be disposed on the strap 360. While an analog watch is depicted in FIG. 3B, one of ordinary skill in the art will recognize that any type of clock may be provided, such as a digital clock.

As can be seen in FIG. 3C, the inner face 370 of the measurement platform 310 is intended to be worn proximate to the wearer's body. A data collection system 380 housed on the measurement platform 310 may include a detector 382, a signal source 384 and a collection magnet 386. As described above, the signal source 384 and the collection magnet 386 may not be provided in all embodiments of the wearable device.

Figure 4A:
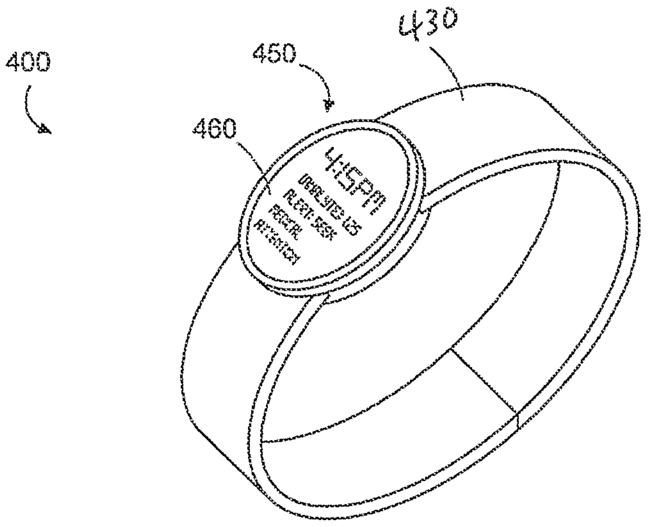
FIG. 4A is a perspective view of an example wrist-mounted device.
Figure 4B:
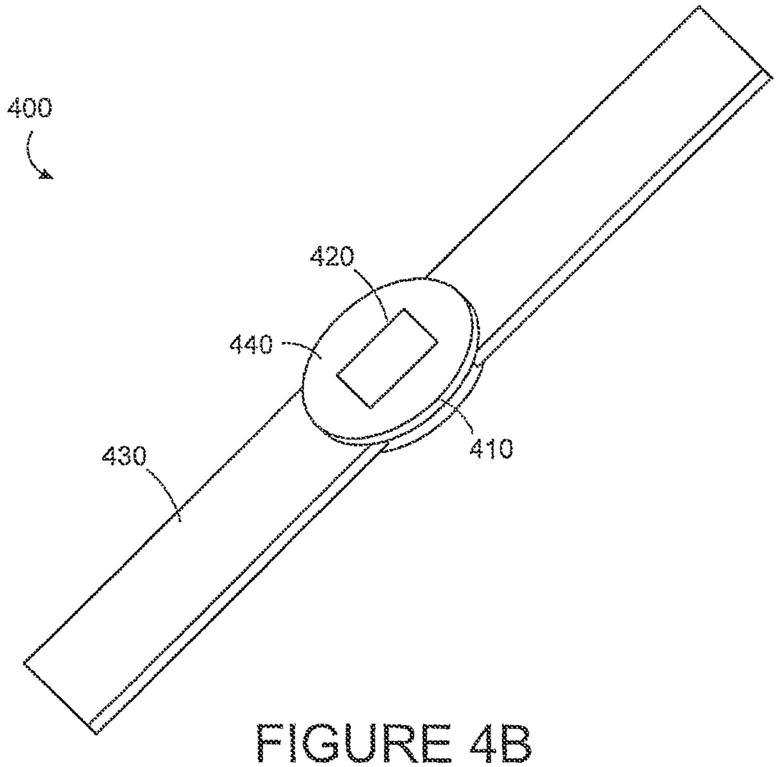
FIG. 4B is a perspective bottom view of an example wrist-mounted device shown in FIG. 4A.

In a further example shown in FIGS. 4A and 4B, a wrist mounted device 400 includes a measurement platform 410, which includes a data collection system 420, disposed on a strap 430. Inner face 440 of measurement platform may be positioned proximate to a body surface so that data collection system 420 may interrogate the subsurface vasculature of the wearer's wrist. A user interface 450 with a display 460 may be positioned facing outward from the measurement platform 410. As described above in connection with other embodiments, user interface 450 may be configured to display data collected from the data collection system 420, including the concentration of one or more measured analytes, and one or more alerts generated by a remote server or other remote computing device, or a processor located on the measurement platform. The user interface 450 may also be configured to display the time of day, date, or other information that may be relevant to the wearer.

Figure 5:
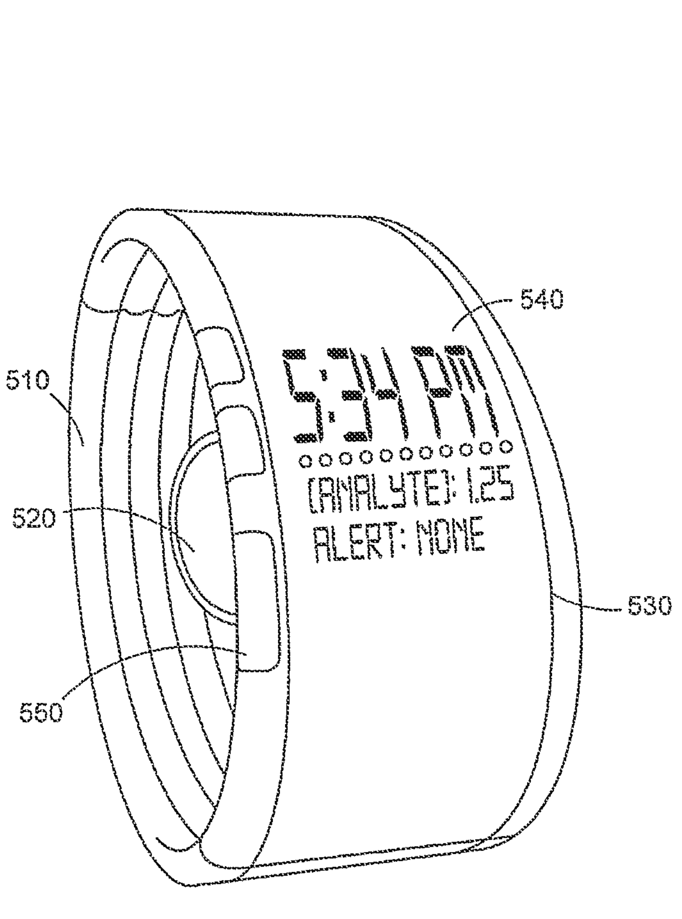
FIG. 5 is a perspective view of an example wrist-mounted device.
Figure 6:
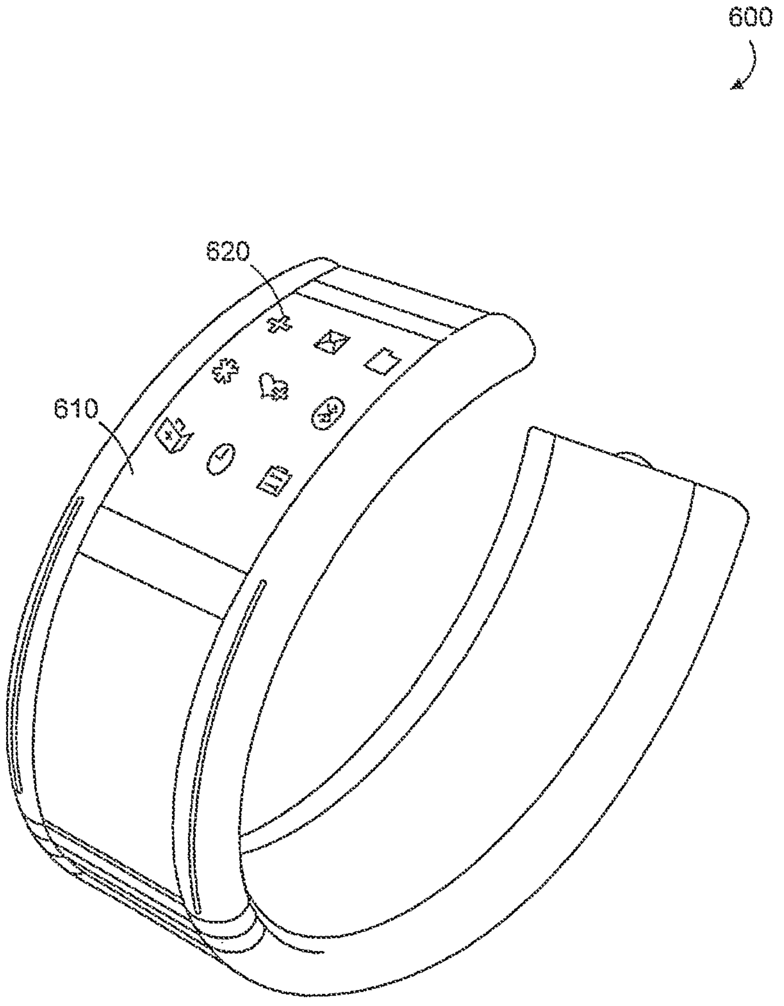
FIG. 6 is a perspective view of an example wrist-mounted device.

As shown in FIG. 5, in a further embodiment, wrist-mounted device 500 may be provided on a cuff 510. Similar to the previously discussed embodiments, device 500 includes a measurement platform 520 and a user interface 530, which may include a display 540 and one or more buttons 550. The display 540 may further be a touch-screen display configured to accept one or more input by the wearer. For example, as shown in FIG. 6, display 610 may be a touch-screen configured to display one or more virtual buttons 620 for accepting one or more inputs for controlling certain functions or aspects of the device 600, or inputs of information by the user, such as current health state.

Figure 7:
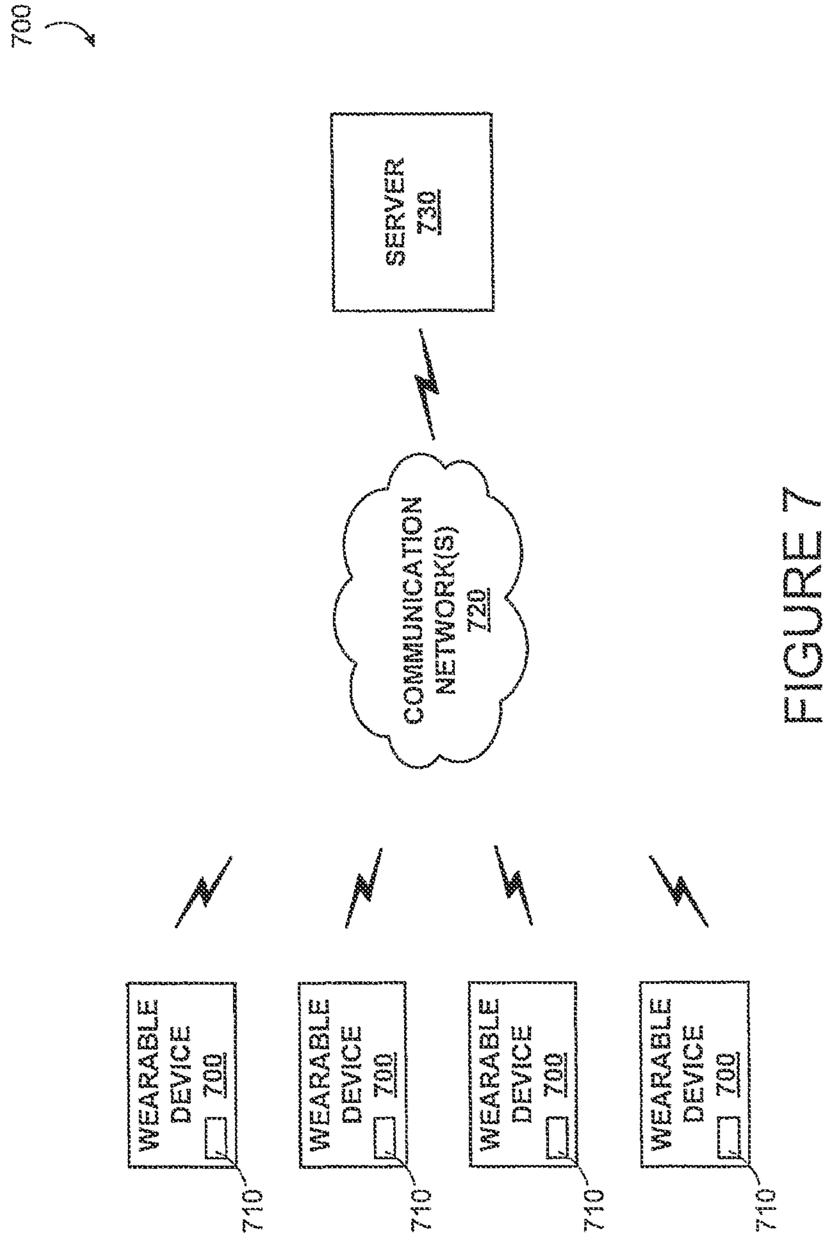
FIG. 7 is a block diagram of an example system that includes a plurality of wearable devices in communication with a server.

FIG. 7 is a simplified schematic of a system including one or more wearable devices 700. The one or more wearable devices 700 may be configured to transmit data via a communication interface 710 over one or more communication networks 720 to a remote server 730. In one embodiment, the communication interface 710 includes a wireless transceiver for sending and receiving communications to and from the server 730. In further embodiments, the communication interface 710 may include any means for the transfer of data, including both wired and wireless communications. For example, the communication interface may include a universal serial bus (USB) interface or a secure digital (SD) card interface. Communication networks 720 may be any one of may be one of: a plain old telephone service (POTS) network, a cellular network, a fiber network and a data network. The server 730 may include any type of remote computing device or remote cloud computing network. Further, communication network 720 may include one or more intermediaries, including, for example wherein the wearable device 700 transmits data to a mobile phone or other personal computing device, which in turn transmits the data to the server 730.

In addition to receiving communications from the wearable device 700, such as collected physiological parameter data and data regarding health state as input by the user, the server may also be configured to gather and/or receive either from the wearable device 700 or from some other source, information regarding a wearer's overall medical history, environmental factors and geographical data. For example, a user account may be established on the server for every wearer that contains the wearer's medical history. Moreover, in some examples, the server 730 may be configured to regularly receive information from sources of environmental data, such as viral illness or food poisoning outbreak data from the Centers for Disease Control (CDC) and weather, pollution and allergen data from the National Weather Service. Further, the server may be configured to receive data regarding a wearer's health state from a hospital or physician. Such information may be used in the server's decision-making process, such as recognizing correlations and in generating clinical protocols.

Additionally, the server may be configured to gather and/or receive the date, time of day and geographical location of each wearer of the device during each measurement period. Such information may be used to detect and monitor spatial and temporal spreading of diseases. As such, the wearable device may be configured to determine and/or provide an indication of its own location. For example, a wearable device may include a GPS system so that it can include GPS location information (e.g., GPS coordinates) in a communication to the server. As another example, a wearable device may use a technique that involves triangulation (e.g., between base stations in a cellular network) to determine its location. Other location-determination techniques are also possible.

The server may also be configured to make determinations regarding the efficacy of a drug or other treatment based on information regarding the drugs or other treatments received by a wearer of the device and, at least in part, the physiological parameter data and the indicated health state of the user. From this information, the server may be configured to derive an indication of the effectiveness of the drug or treatment. For example, if a drug is intended to treat nausea and the wearer of the device does not indicate that he or she is experiencing nausea after beginning a course of treatment with the drug, the server may be configured to derive an indication that the drug is effective for that wearer. In another example, a wearable device may be configured to measure blood glucose. If a wearer is prescribed a drug intended to treat diabetes, but the server receives data from the wearable device indicating that the wearer's blood glucose has been increasing over a certain number of measurement periods, the server may be configured to derive an indication that the drug is not effective for its intended purpose for this wearer.

Further, some embodiments of the system may include privacy controls which may be automatically implemented or controlled by the wearer of the device. For example, where a wearer's collected physiological parameter data and health state data are uploaded to a cloud computing network for trend analysis by a clinician, the data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined.

Additionally or alternatively, wearers of a device may be provided with an opportunity to control whether or how the device collects information about the wearer (e.g., information about a user's medical history, social actions or activities, profession, a user's preferences, or a user's current location), or to control how such information may be used. Thus, the wearer may have control over how information is collected about him or her and used by a clinician or physician or other user of the data. For example, a wearer may elect that data, such as health state and physiological parameters, collected from his or her device may only be used for generating an individual baseline and recommendations in response to collection and comparison of his or her own data and may not be used in generating a population baseline or for use in population correlation studies.

III. Example Electronics Platform for a Wearable Device

Figure 8:
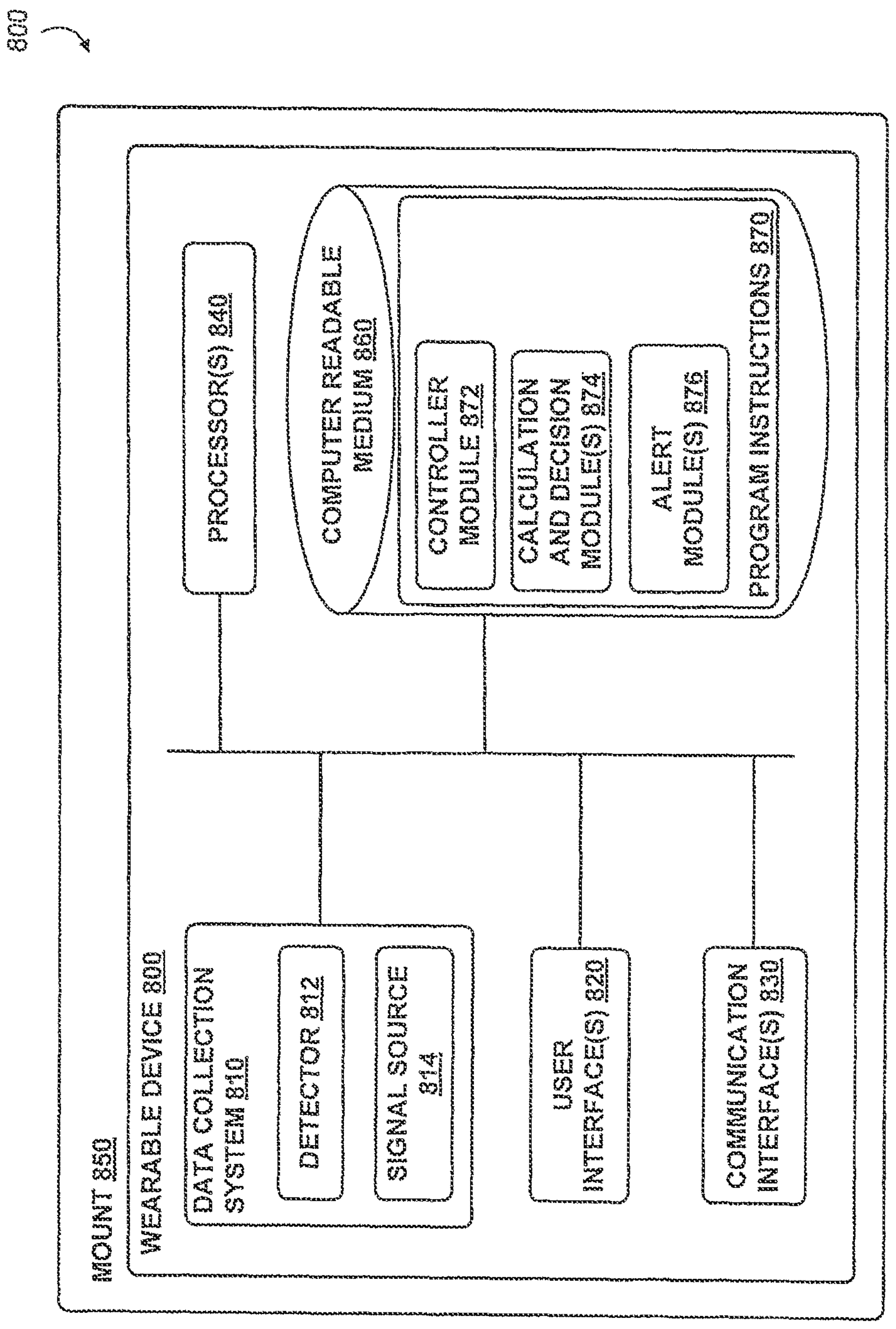
FIG. 8 is a functional block diagram of an example wearable device.

FIG. 8 is a simplified block diagram illustrating the components of a wearable device 800, according to an example embodiment. Wearable device 800 may take the form of or be similar to one of the wrist-mounted devices 200, 300, 400, 500, 600, shown in FIGS. 2A-B, 3A-3C, 4A-4C, 5 and 6. However, wearable device 800 may also take other forms, such as an ankle, waist, or chest-mounted device.

In particular, FIG. 8 shows an example of a wearable device 800 having a data collection system 810, a user interface 820, communication platform 830 for transmitting data to a server, and processor(s) 840. The components of the wearable device 800 may be disposed on a mount 850 for mounting the device to an external body surface where a portion of subsurface vasculature is readily observable.

Processor 840 may be a general-purpose processor or a special purpose processor (e.g., digital signal processors, application specific integrated circuits, etc.). The one or more processors 840 can be configured to execute computer-readable program instructions 870 that are stored in the computer readable medium 860 and are executable to provide the functionality of a wearable device 800 described herein.

The computer readable medium 860 may include or take the form of one or more non-transitory, computer-readable storage media that can be read or accessed by at least one processor 840. The one or more computer-readable storage media can include volatile and/or non-volatile storage components, such as optical, magnetic, organic or other memory or disc storage, which can be integrated in whole or in part with at least one of the one or more processors 840. In some embodiments, the computer readable medium 860 can be implemented using a single physical device (e.g., one optical, magnetic, organic or other memory or disc storage unit), while in other embodiments, the computer readable medium 860 can be implemented using two or more physical devices.

Data collection system 810 includes a detector 812 and, in some embodiments, a signal source 814. As described above, detector 812 may include any detector capable of detecting at least one physiological parameter, which could include any parameters that may relate to the health of the person wearing the wearable device. For example, the detector 812 could be configured to measure blood pressure, pulse rate, skin temperature, etc. At least one of the detectors 812 is configured to non-invasively measure one or more analytes in blood circulating in subsurface vasculature proximate to the wearable device. In some examples, detector 812 may include one or more of an optical (e.g., CMOS, CCD, photodiode), acoustic (e.g., piezoelectric, piezoceramic), electrochemical (voltage, impedance), thermal, mechanical (e.g., pressure, strain), magnetic, or electromagnetic (e.g., magnetic resonance) sensor.

In some examples, the data collection system 810 further includes a signal source 814 for transmitting an interrogating signal that can penetrate the wearer's skin into the portion of subsurface vasculature. In general, signal source 814 will generate an interrogation signal that will produce a responsive signal that can be detected by one or more of the detectors 812. The interrogating signal can be any kind of signal that is benign to the wearer, such as electromagnetic, magnetic, optic, acoustic, thermal, mechanical, and results in a response signal that can be used to measure a physiological parameter or, more particularly, that can detect the binding of the clinically-relevant analyte to the antibody-particle conjugates. In one example, the interrogating signal is an electromagnetic pulse (e.g., a radio frequency (RF) pulse) and the response signal is a magnetic resonance signal, such as nuclear magnetic resonance (NMR). In another example, the interrogating signal is a time-varying magnetic field, and the response signal is an externally-detectable physical motion due to the time-varying magnetic field. The time-varying magnetic field modulates the particles by physical motion in a manner different from the background, making them easier to detect. In a further example, the interrogating signal is an electromagnetic radiation signal. In particular, the interrogating signal may be electromagnetic radiation having a wavelength between about 400 nanometers and about 1600 nanometers. The interrogating signal may, more particularly, comprise electromagnetic radiation having a wavelength between about 500 nanometers and about 1000 nanometers. In examples where the antibody-particle conjugates include a fluorophore, the interrogating signal may therefore be an electromagnetic radiation signal with a wavelength that can excite the fluorophore and penetrate the skin or other tissue and subsurface vasculature (e.g., a wavelength in the range of about 500 to about 1000 nanometers), and the response signal is fluorescence radiation from the fluorophore that can penetrate the subsurface vasculature and tissue to reach the detector.

The program instructions 870 stored on the computer readable medium 860 may include instructions to perform or facilitate some or all of the device functionality described herein. For instance, in the illustrated embodiment, program instructions 870 include a controller module 872, calculation and decision module 874 and an alert module 876.

The controller module 872 can include instructions for operating the data collection system 810, for example, the detector 812 and signal source 814. For example, the controller 872 may activate signal source 814 and/or detector 812 during each of the pre-set measurement periods. In particular, the controller module 872 can include instructions for controlling the signal source 814 to transmit an interrogating signal at preset measurement times and controlling the detector 812 to receive data representative of response signals transmitted from the portion of subsurface vasculature in response to the interrogating signals transmitted at the preset measurement times.

The controller module 872 can also include instructions for operating a user interface 820. For example, controller module 872 may include instructions for displaying data collected by the data collection system 810 and analyzed by the calculation and decision module 874, or for displaying one or more alerts generated by the alert module 875. Further, controller module 872 may include instructions to execute certain functions based on inputs accepted by the user interface 820, such as inputs accepted by one or more buttons disposed on the user interface.

Communication platform 830 may also be operated by instructions within the controller module 872, such as instructions for sending and/or receiving information via a wireless antenna, which may be disposed on or in the wearable device 800. The communication interface 830 can optionally include one or more oscillators, mixers, frequency injectors, etc. to modulate and/or demodulate information on a carrier frequency to be transmitted and/or received by the antenna. In some examples, the wearable device 800 is configured to indicate an output from the processor by modulating an impedance of the antenna in a manner that is perceivable by a remote server or other remote computing device.

Calculation and decision module 872 may include instructions for receiving data from the data collection system 810 in the form of a responsive signal, analyzing the data to determine if the target analyte is present or absent, quantify the measured physiological parameter(s), such as concentration of a target analyte, and analyzing the data to determine if a medical condition is indicated. In particular, the calculation and decision module 872 may include instructions for determining, for each preset measurement time, a concentration of a clinically-relevant analyte based on the response signal detected by the detector at that measurement time and determining, for each preset measurement time, whether a medical condition is indicated based on at least the corresponding concentration of the clinically-relevant analyte. The preset measurement times may be set to any period and, in one example, are about one hour apart.

The program instructions of the calculation and decision module 872 may, in some examples, be stored in a computer-readable medium and executed by a processor located external to the wearable device. For example, the wearable device could be configured to collect certain data regarding physiological parameters from the wearer and then transmit the data to a remote server, which may include a mobile device, a personal computer, the cloud, or any other remote system, for further processing.

The computer readable medium 860 may further contain other data or information, such as medical and health history of the wearer of the device, that may be useful in determining whether a medical condition is indicated. Further, the computer readable medium 860 may contain data corresponding to certain analyte baselines, above or below which a medical condition is indicated. The baselines may be pre-stored on the computer readable medium 860, may be transmitted from a remote source, such as a remote server, or may be generated by the calculation and decision module 874 itself. The calculation and decision module 874 may include instructions for generating individual baselines for the wearer of the device based on data collected over a certain number of measurement periods. For example, the calculation and decision module 874 may generate a baseline concentration of a target blood analyte for each of a plurality of measurement periods by averaging the analyte concentration at each of the measurement periods measured over the course of a few days, and store those baseline concentrations in the computer readable medium 860 for later comparison. Baselines may also be generated by a remote server and transmitted to the wearable device 800 via communication interface 830. The calculation and decision module 874 may also, upon determining that a medical condition is indicated, generate one or more recommendations for the wearer of the device based, at least in part, on consultation of a clinical protocol. Such recommendations may alternatively be generated by the remote server and transmitted to the wearable device.

In some examples, the collected physiological parameter data, baseline profiles, health state information input by device wearers and generated recommendations and clinical protocols may additionally be input to a cloud network and be made available for download by a wearer's physician. Trend and other analyses may also be performed on the collected data, such as physiological parameter data and health state information, in the cloud computing network and be made available for download by physicians or clinicians.

Further, physiological parameter and health state data from individuals or populations of device wearers may be used by physicians or clinicians in monitoring efficacy of a drug or other treatment. For example, high-density, real-time data may be collected from a population of device wearers who are participating in a clinical study to assess the safety and efficacy of a developmental drug or therapy. Such data may also be used on an individual level to assess a particular wearer's response to a drug or therapy. Based on this data, a physician or clinician may be able to tailor a drug treatment to suit an individual's needs.

In response to a determination by the calculation and decision module 874 that a medical condition is indicated, the alert module 876 may generate an alert via the user interface 820. The alert may include a visual component, such as textual or graphical information displayed on a display, an auditory component (e.g., an alarm sound), and/or tactile component (e.g., a vibration). The textual information may include one or more recommendations, such as a recommendation that the wearer of the device contact a medical professional, seek immediate medical attention, or administer a medication.

Figure 9:
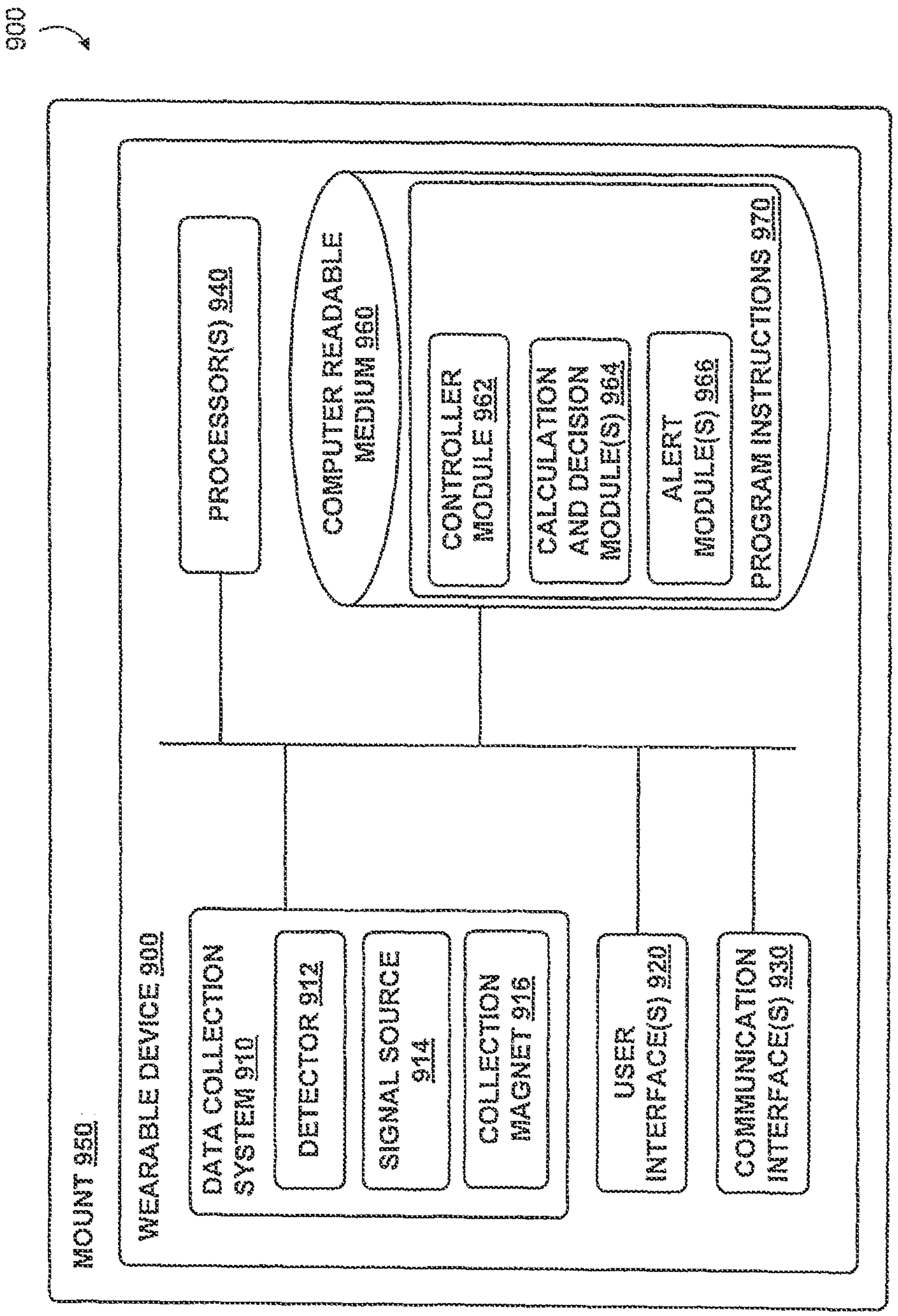
FIG. 9 is a functional block diagram of an example wearable device.
Figure 1C:
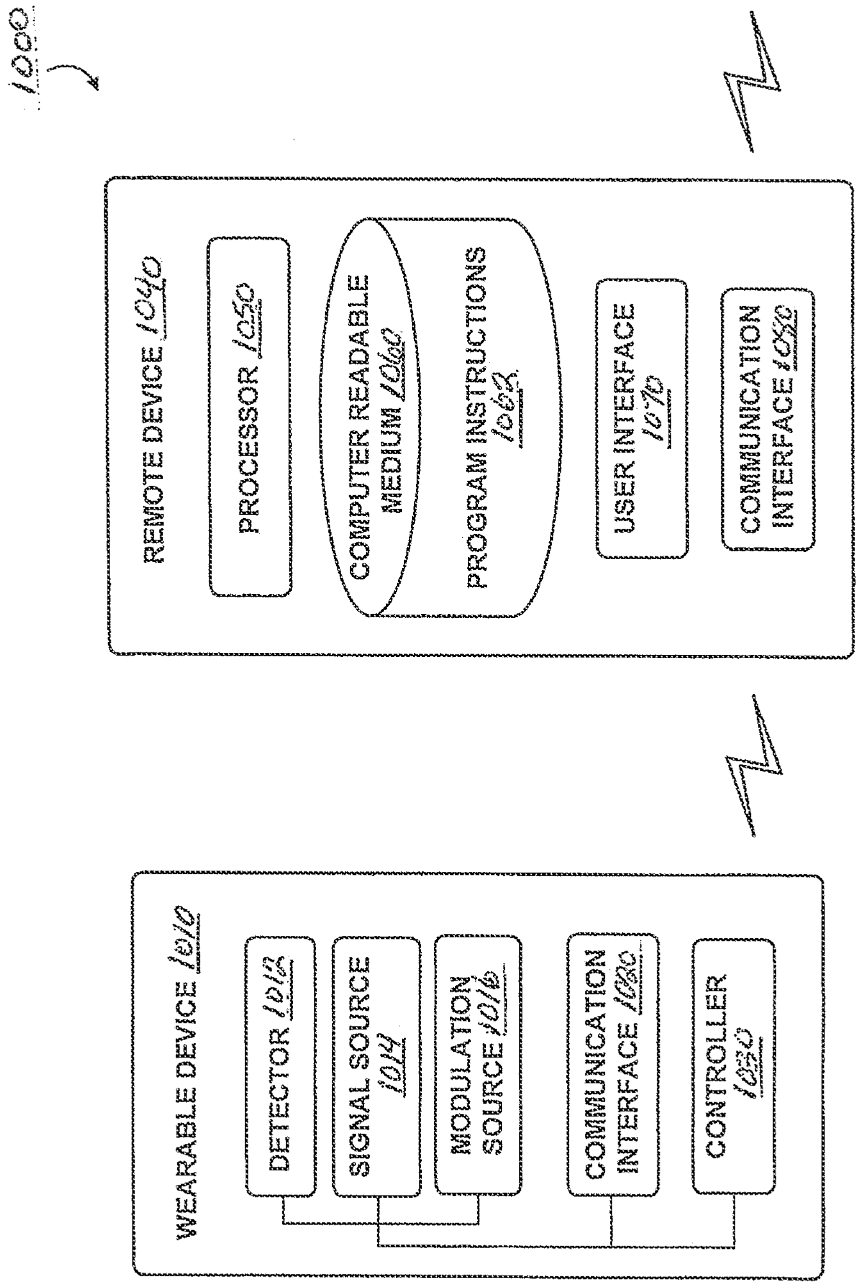

FIG. 9 is a simplified block diagram illustrating the components of a wearable device 900, according to an example embodiment. Wearable device 900 is the same as wearable device 800 in all respects, except that the data collection system 910 of wearable device 900 further includes a collection magnet 916. In this example, the collection magnet 916 may be used to locally collect antibody—magnetic particles conjugates present in an area of subsurface vasculature proximate to the collection magnet 916. As described above, collection magnet 916 is configured to direct a magnetic field into a portion of subsurface vasculature sufficient to cause the antibody—magnetic particles conjugates to collect in a lumen of the portion of subsurface vasculature.

Wearable device 900 includes a data collection system 910, which includes a detector 912, a signal source 914 (if provided) and a collection magnet 916, a user interface 920, a communication interface 930, a processor 940 and a computer readable medium 960 on which program instructions 970 are stored. All of the components of wearable device 900 may be provided on a mount 950. In this example, the program instructions 970 may include a controller module 962, a calculation and decision module 964 and an alert module 966 which, similar to the example set forth in FIG. 8, include instructions to perform or facilitate some or all of the device functionality described herein. Controller module 962 further includes instructions for operating collection magnet 916. For example, controller module 962 may include instructions for activating collection magnet during a measurement period, for a certain amount of time.

FIG. 10 is a simplified block diagram illustrating the components of an example system 1000, including a wearable device 1010. Wearable device 1010 may take the form of or be similar to one of the wrist-mounted devices 200, 300, 400, 500, or 600, shown in FIGS. 2A-B, 3A-3C, 4A-4C, 5, and 6. However, wearable device 1010 may also take other forms, such as an ankle, waist, ear, eye or chest-mounted device. Further, any of devices 200, 300, 400, 500, and 600 may be configured similar to or include any of the components of system 1000, including wearable device 1010.

In particular, FIG. 10 shows an example of a system 1000 including a wearable device 1010 having a detector 1012, in some examples, a signal source 1014, a modulation source 1016, and a communication interface 1020, controlled by a controller 1030. Communication interface 1020 may include an antenna. The components of the wearable device 1010 may be disposed on a mount (not shown) for mounting the device to an external body surface where a portion of subsurface vasculature is readily observable. System 1000 may further include a remote device 1040 in communication with the wearable device 1010, including a processor 1050, a computer readable medium 1060, a user interface 1070, and a communication interface 1080 for communicating with the wearable device 1010 and/or for transmitting data to a server or other remote computing device. While FIG. 10 depicts various components of system 1000 disposed on the wearable device 1010 or the remote device 1040, one of ordinary skill in the art would understand that different configurations and designs are possible, including where all of the components are provided on the wearable device.

Processor 1050 may be a general-purpose processor or a special purpose processor (e.g., digital signal processors, application specific integrated circuits, etc.) and can be configured to execute computer-readable program instructions 1062 that are stored in the computer readable medium 1060 and are executable to provide the functionality of a system 1000 as described herein. The computer readable medium 1060 may include or take the form of one or more non-transitory, computer-readable storage media that can be read or accessed by the processor 1050, and can include volatile and/or non-volatile storage components, such as optical, magnetic, organic or other memory or disc storage, which can be integrated in whole or in part with the processor 1050. The controller 1030 may be configured to operate one or more of the detector 1012, signal source 1014 and modulation source 1016. For example, the controller 1030 may activate the detector 1012, signal source 1014 and modulation source 1016 during each of the pre-set measurement periods.

The program instructions 1062 stored on the computer readable medium 1060 may include instructions to perform or facilitate some or all of the system functionality described herein. For instance, in the illustrated embodiment, program instructions 1062 may include instructions for controller 1030 to operate the detector 1012, signal source 1014 and modulation source 1016. Program instructions 1062 may further cause the processor 1050 to detect the one or more target analytes by differentiating the analyte response signal from the background signal based, at least in part, on a modulation applied by the modulation source 1016. In some cases, the processor may further be configured to differentiate the analyte response signal from the unbound particle signal. Further, the processor 1050 may be configured to determine the concentration of a particular target analyte in the blood from, at least in part, the analyte response signal. The detection and concentration data processed by the processor may be communicated to the patient, for example via the user interface 1070, transmitted to medical or clinical personnel, locally stored or transmitted to a remote server, the cloud, and/or any other system where the data may be stored or accessed at a later time. The program instructions 1062 may also include instructions for operating a user interface 1070, for example, instructions for displaying data transmitted from the wearable device 1010 and analyzed by the processor 1050, or for generating one or more alerts.

IV. Illustrative Antibody—Particle Conjugates

In some examples, the wearable devices described above obtain at least some of the health-related information by detecting the binding of a clinically-relevant analyte to antibody-conjugated particles. The particles could be, for example, microparticles or nanoparticles. The particles can be functionalized by covalently attaching a complex of a fluorophore-labeled antibody and quencher-labeled protein M designed to selectively bind or otherwise recognize a particular clinically-relevant analyte. The labeled protein M binds nons-specifically to the target analyte binding site of the antibody and can be competitively displaced by the target analyte in solution. Labeled protein M can be used as a generic ligand to the labeled antibody to form the complex, thus advantageously eliminating the need to label specific target molecules to each antibody in a homogenous FRET-based assay. The particles may be functionalized with one or more antibodies to increase avidity to a target analyte or to detect multiple different targets. The antibody-particle conjugates can be introduced into the person's blood stream by injection, ingestion, inhalation, transdermally, or in some other manner.

A. Definitions

Generally, the nomenclature used herein and many of the fluorescence, luminescence, and chemical reactions, and enzymatic reactions described herein are commonly employed. See, generally, Lakowicz, J. R. *Topics in Fluorescence Spectroscopy,* (3 volumes) New York: Plenum Press (1991), and Lakowicz, J. R. *Emerging applications of florescence spectroscopy to cellular imaging: lifetime imaging, metal-ligand probes, multi photon excitation and light quenching*, Scanning Microsc. Suppl. Vol. 10 (1996) pages 213-24, for fluorescence techniques; Sambrook et al., *Molecular Cloning: A Laboratory Manual,* 2ed. (1989) Cold Spring Harbor Laboratory Press, Cold Spring Harbor, N.Y., for molecular biology methods; Cells: A Laboratory Manual, 1$^{st}$ edition (1998) Cold Spring Harbor Laboratory Press, Cold Spring Harbor, N.Y., for cell biology methods; and *Optics Guide*5 Melles Griot® Irvine Calif., and *Optical Waveguide Theory*, Snyder & Love (published by Chapman & Hall) for general optical methods, all of which are incorporated herein by reference.

General methods for performing a variety of fluorescent or luminescent assays are described in, e.g., Lakowicz, J. R., Topics in Fluorescence Spectroscopy, volumes 1 to 3, New York: Plenum Press (1991); Herman, B., Resonance Energy Transfer Microscopy, in Fluorescence Microscopy of Living Cells in Culture, Part B, Methods in Cell Biology, vol. 30, ed. Taylor, D. L. & Wang, Y.-L., San Diego: Academic Press (1989), pp. 219-243; Turro, N.J., Modern Molecular Photochemistry, Menlo Park: Benjamin/Cummings Publishing Col, Inc. (1978), pp. 296-361; and Bernard Valeur, "Molecular Fluorescence: Principles and Applications" Wiley VCH, 2002. Guidance in the selection and use of specific resonance acceptor moieties is available at, for example, Berlman, I. B., Energy transfer parameters of aromatic compounds, Academic Press, New York and London (1973), which contains tables of spectral overlap integrals for the selection of resonance energy transfer pairs. Additional information sources include the Molecular Probes Catalog (2003) and website; and Tsien et al., 1990 Handbook of Biological Confocal Microscopy, pp. 169-178.

The term "FRET" means "fluorescence resonance energy transfer" or "Forster resonance energy transfer", and refers to the radiationless transmission of an energy quantum from its site of absorption (the donor) to the site of its utilization (the acceptor) in a molecule, or system of molecules, by resonance interaction between light sensitive molecules (chromophores), e.g., donor and acceptor species or chromophores, over distances considerably greater than interatomic, without substantial conversion to thermal energy, and without the donor and acceptor coming into kinetic collision. A "donor" is a moiety that initially absorbs energy (e.g., optical energy or electronic energy). Generally, the donor and acceptor species are different, in which case FRET can be detected by the appearance of fluorescence of the acceptor or by quenching of donor fluorescence.

The detection and quantitation of FRET can be accomplished in a number of different ways. Because FRET can result in both a decrease in fluorescence of the donor molecule as well as an increase in fluorescence of the acceptor, a ratio metric determination of the two signals can be made. The advantage of this method is that a measure of interaction can be made that is independent of the absolute concentration of the sensor. Because not all acceptor moieties are fluorescent, they can be used as a means to quench fluorescence. In these instances, those interactions that result in a fluorescent donor molecule coming in close proximity to such a molecule would result in a loss of signal. Inversely, reactions that remove the proximity of a fluorescent donor and a quencher would result in an increase in fluorescence.

A "FRET response," which may be described as a "FRET signal" or "signal," generally comprises any measurable signal(s) indicative of FRET. The FRET response may be measured in any suitable manner, including illumination with excitation light, detection of one or more emission signals, and performance of mathematical operations on the one or more emission signals. For example, if the FRET acceptor is fluorescent, the FRET response may be measured as an increase in emission intensity from the acceptor at a wavelength (or wavelength range) of acceptor emission. If the FRET acceptor is a quencher, then the FRET response may be measured as an absence or decrease in the emission intensity from the donor at a wavelength (or wavelength range) of donor emission.

The term "acceptor" refers to a chemical or biological moiety that accepts energy via resonance energy transfer. In FRET applications, acceptors may re-emit energy transferred from a donor fluorescent or luminescent moiety as fluorescence and are "fluorescent acceptor moieties." As used herein, such a donor fluorescent or luminescent moiety and an acceptor fluorescent moiety are referred to as a "FRET pair." Examples of acceptors include coumarins and related fluorophores; xanthenes such as fluoresceins and fluorescein derivatives; fluorescent proteins such as GFP and GFP derivatives; rhodols, rhodamines, and derivatives thereof; resorufins; cyanines; difluoroboradiazaindacenes; and phthalocyanines acceptors, including fluorescent acceptor moieties.

The term "quencher" refers to a type of acceptor that does not re-emit energy and functions to quence the fluorescence of a proximate fluorophore. Many organic dyes may be used as quenchers in FRET bioassays as long as the spectrally matched fluorophore-quencher pairs can be brought to close proximity with proper alignment. However, many organic dyes which might be used as quenchers have intrinsic fluorescence, which can result in an undesirable high background fluorescence (through energy transfer) and hence attenuate the sensitivity of FRET assays. Dark quenchers with little or no intrinsic fluorescence can efficiently quench the fluorescence from the proximate fluorophores with little background and can be used in the methods herein. Of many dark quenchers, 4-(4' dimethylaminophenylazo)benzoic acid (DABCYL) is a common dark quencher used widely in many assays, such as "molecular beacons" for DNA detection (U.S. Pat. No. 5,989,823); Diazo dyes of the BHQ series, which are referred to as "Black Hole Quenchers" (International Patent Publication No. WO 01/86001), provide a broad range of absorption which overlaps well with the emission of many fluorophores; the QSY series dyes are another series of useful dark quenchers used extensively as quenching reagents in many bioassays (U.S. Pat. No. 6,399,392), which is incorporated by reference in its entirety; a class of relatively water-soluble dyes is the non-fluorescent asymmetric cyanine dye series (See, for example, U.S. Pat. No. 6,348,596); and other useful dark quenchers for use in FRET assays include non-fluorescent dyes described in US Patent publication no. 2005/0118619, all which are incorporated by reference in its entirety.

A "binding complex" or "complex" generally comprises a complex formed by binding of a corresponding pair of binding partners such as an antibody/antigen or receptor/ligand to one another. Accordingly, the binding complex may be formed with substantial specificity and affinity, and generally results in noncovalent association of the binding partners with one another.

The term "conjugated" generally characterizes direct attachment of a member (eg, a FRET member, binding partner, a surface of a solid support such as a particle, etc.) of a FRET assay system to another member of the system, or indirect attachment of the members via a bridge (eg, a solid support, a linker, and/or the like). The attachment may be covalent, which may be through a chemical bond or an uninterrupted series of two or more chemical bonds (and intervening one or more atoms) extending, collectively, from one member to the other. Accordingly, members may be connected covalently by formation of at least one chemical bond between the members. Alternatively, the attachment may, at least in part, be through (a) a binding interaction of a corresponding pair of binding partners each included in a member or disposed generally between the members, (b) nonspecific interactions between the members themselves or at least one or both of the members and a bridge (e.g., protein adsorption to a solid support surface), and/or (c) entrapment of one of the members within the other member. Connection of a member(s) (eg, a FRET member and/or a binding member) to the surface of a solid support may form a modified surface of the solid support.

Various strategies may be utilized to connect a binding partner such as an antibody to the surface of a solid support such as a particle. For example, the binding partner can be immobilized directly through formation of a chemical bond between the surface and the binding partner, e.g., an amino group on a protein such as an antibody can be linked to a carboxyl group on a polymer surface. In other cases, the binding partner alternatively can be adsorbed to a solid phase surface through noncovalent interactions. Alternatively, or in addition, the binding partner may be immobilized with respect to the surface indirectly. For example, a binding partner modified with biotin can be immobilized on a surface modified with streptavidin through a biotin/streptavidin interaction.

A "surface" generally comprises an external interface, or portion thereof, of a solid support such as a particle, e.g., nanoparticle or microparticle.

A "target analyte" or "analyte" generally comprises any substance undergoing analysis in a FRET binding assay. The analyte may be analyzed to determine its amount (e.g., presence/absence, concentration, quantity (such as number of moles/molecules), relative increase/decrease in concentration or quantity, relationship to a threshold level, etc.) in a sample or in bodily fluid, e.g., blood or perspiration. Alternatively, or in addition, the analyte may be analyzed to determine an activity (e.g, inhibition/activation of a chemical reaction, such as an enzyme-catalyzed reaction) of another analyte in a sample. The other analyte may be one or more members of a library of compounds being screened in a plurality of samples. Exemplary analytes may include inorganic substances, small organic molecules, biopolymers, or the like. Accordingly, analytes may include inorganic ions, nucleic acids (monomers or polymers), amino acids, peptides, proteins, lipids, carbohydrates, metabolites or the like. In some embodiments, the analyte may be a reactant or a product of a chemical reaction performed in a sample/assay solution. The chemical reaction may be catalyzed by an enzyme in the sample and thus the analyte may be a substrate or a product of an enzyme-catalyzed reaction performed in the sample.

Terms describing molecular-scale members of an assay system, such as "a FRET member," "a FRET pair," "a binding partner," "a binding complex," and "a chain," are used in the singular in the present disclosure for clarity and simplification. However, each term may represent many individual moieties, molecules, and/or complexes, of the molecular-scale member.

B. Detection Probe

In one embodiment, a composition for use as a detection probe in a homogeneous competitive displacement FRET method for detection of target analytes in one step is provided. The composition can be used as a detection probe for in vivo or in vitro detection of target analytes in solution, e.g., bodily fluid. The composition includes at least one particle labeled with at least one complex of a labeled-antibody and labeled-protein M ("Mq"). Protein M binds to a human antibody binding site and competes non-specifically for access to the antibody combining site.

Figure 11:
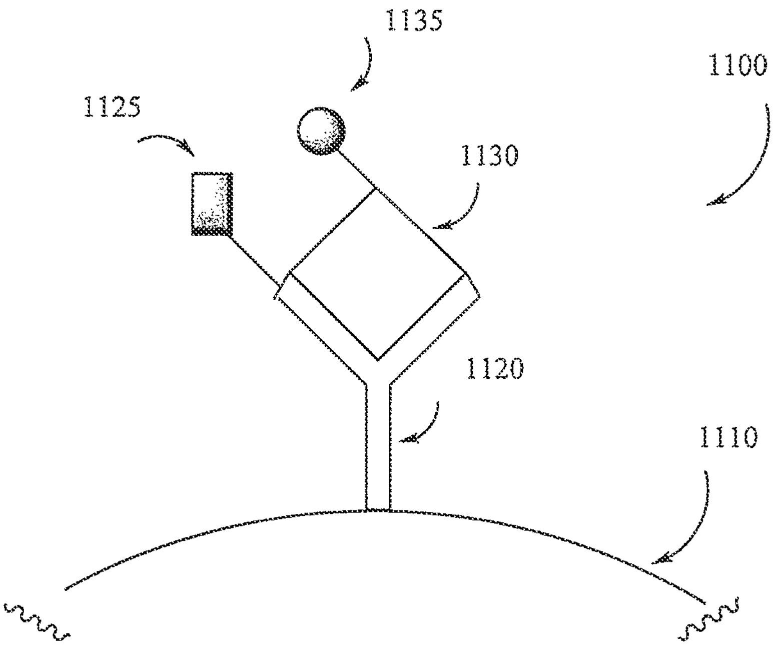
FIG. 11 illustrates an example detection probe.

In one embodiment as shown in FIG. 11, the detection probe 1100 includes a particle 1110 such as a nanoparticle that is conjugated to a complex of an antibody 1120 labeled with a fluorophore 1125 and protein M 1130 labeled with a quencher (Mq) 1135. As defined herein, a "fluorophore" is a molecule (e.g., colored dye) which emits light at a specific range of wavelengths or segment of the spectrum after excitation by light of a lower wavelength or lower range of wavelengths versus the emission wavelengths. Different types of fluorophores emit energy at different wavelengths or spectral ranges. As defined herein, a "quencher" is a molecule which absorbs light energy (or photons) at a specific spectral range of wavelengths and does not re-emit light, but converts virtually all of the excitation light energy into invisible vibrations (e.g., infrared or heat). Different types of quenchers absorb energy at different wavelengths or spectral ranges. By placing the fluorophore of the antibody and quencher of protein at a suitable proximity between each other, the fluorophore can be "quenched" by the quencher. Once Mq 1130 is displaced or removed from the proximity of the fluorophore-labeled antibody 1120 by competitive displacement of Mq 1130 from the fluorophore-labeled antibody 1120 by a target analyte at a certain concentration in a solution, the fluorophore is no longer quenched and can emit detectable energy after photoexcitation. The degree of displacement of Mq 1130 depends upon the concentration of the target analyte in the solution. Therefore, measurement of the amount of fluorescence generated, when suitably calibrated, provides a quantitative measure of the concentration of target analyte.

Figure 12:
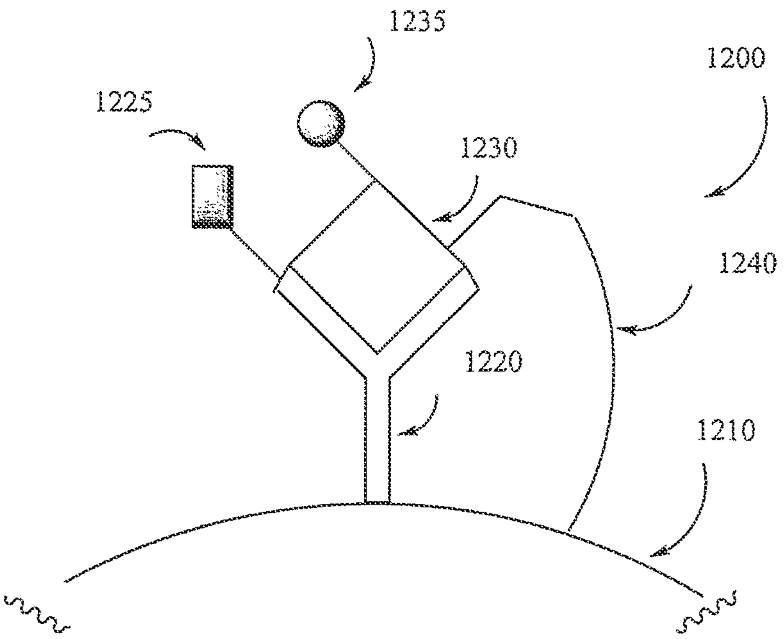
FIG. 12 illustrates an example detection probe.
Figure 13:
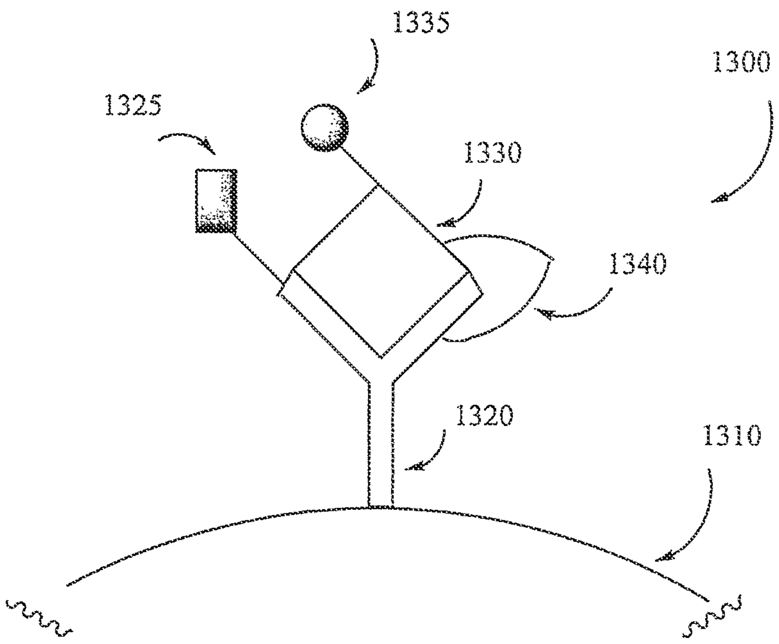
FIG. 13 illustrates an example detection probe.

In another embodiment as shown in FIG. 12, a composition 1200 is provided which includes a particle 1210 such as a nanoparticle that is conjugated to a complex of an antibody 1220 labeled with a fluorophore 1225 and protein M 1230 labeled with a quencher (Mq) 1235. Quencher-labeled protein M 1230 is tethered 1240 to the surface of nanoparticle 1210 so that displacement of Mq 1230 by a target analyte is reversible. In this embodiment as shown in FIG. 12, Protein M 1230 can be engineered with a sufficiently low affinity and is covalently tethered via a linker 1240 of a suitable length to the surface of a support 1210 such as a particle, e.g., nanoparticle. Alternatively as shown in FIG. 13, a detection probe 1300 bound to a surface of a particle 1310 and including a protein M 1330 labeled with a quencher 1335 can be covalently tethered via a linker 1330 to the antibody 1330 as shown in FIG. 13. In either arrangement shown in FIGS. 12 and 13, Mq (1230, 1330) can be competitively displaced off the antibody combining site on the antibody in the presence of the target analyte at a certain concentration in vivo but the tether (1240, 1340) prevents the quencher-labeled protein M (1230, 1330) from diffusing away. Upon suitable change in assay conditions, the tethered quencher-labeled protein M (1230, 1330) in the detection agent (1200, 1300) can displace the target analyte, regenerating the detection agent (1200, 1300) for future use.

C. Protein M

Protein M, also referred to as MG281 protein, is a class of antigen derived from mycoplasma, a genus of bacteria that includes species that are pathogenic to humans. Protein M or fragments thereof were found to bind non-specifically to immunoglobulins with high affinity and compete non-specifically for access to the antibody combining site (1). Protein M and fragments were used for purifying or isolating immunoglobins as well as in vaccines as treatment against mycoplasma infections, myeloma as well as autoimmune disease. The sequence, preparation, purification and isolation of protein M and fragments thereof recombinantly or from mycobacteria are described in WO 2014/014897 and Grover et al., Science, 2014, Vol. 343, pp. 656-661, which is incorporated by reference in its entirety. Recombinant Protein M having various pre-determined binding specificity and affinity can be generated by any suitable method. In a representative example for generating protein M, *E. coli* BL21 can be transfected with a suitable plasmid encoding protein M or a fragment thereof wherein the expression can be induced by the addition of a suitable agent, e.g., isopropyl B-D-1-thiogalactopyranoside. The transfected cells is then harvested, lysed, and the resultant recombinant protein is then purified by affinity chromatography.

D. Antibodies

The antibodies of the present invention may belong to any antibody class, including for example, IgG, IgM, IgA, IgD and IgE, and may be prepared by any of a variety of techniques known to the skilled artisan. (See, e.g., Dean, *Methods Mol. Biol.* 80:23-37 (1998); Dean, *Methods Mol. Biol.* 32:361-79 (1994); Baileg, *Methods Mol. Biol.* 32:381-88 (1994); Gullick, *Methods Mol. Biol.* 32:389-99 (1994); Drenckhahn et al. *Methods Cell. Biol.* 37:7-56 (1993); Morrison, *Ann. Rev. Immunol.* 10:239-65 (1992); Wright et al. *Crit. Rev. Immunol.* 12:125-68 (1992); Harlow and Lane, *Antibodies: A Laboratory Manual*, Cold Spring Harbor Laboratory (1988); and *Making and Using Antibodies: A Practical Handbook*, Howard and Kaser, eds., CRC Press (2006), each one of which is incorporated herein by reference in its entirety.)

The antibodies of the invention also may be a single chain antibody (scFv), or an antigen binding fragment of an antibody. Antigen-binding fragments of antibodies are a portion of an intact antibody comprising the antigen binding site or variable region of an intact antibody, wherein the portion is free of the constant heavy chain domains of the Fc region of the intact antibody. Examples of antibody fragments include Fab, Fab', Fab'-SH, $F(ab')_2$ and $F_v$ fragments. In addition to production and purification from animals or mammalian cells, antibodies, antibody fragments, or nonantibody scaffolds can be selected based upon various in vitro technologies, including phage display, ribosomal display, or bacterial display.

E. Protein Labeling with a Fluorophore or Quencher

Fluorophore (or quencher) labeling of a protein target molecule such as an antibody or protein M for use as specific detection probes for the detection of target analytes generally involves the process of covalently attaching a label to the target protein molecule. The process is generally accomplished using a reactive derivative of a fluorophore (or quencher) that selectively binds to a functional group contained in the protein target molecule. Common reactive groups include iosthiocyanate derivatives such as FITC and TRITC (derivatives of fluorescenine and rhodamine) are reactive towards primary amenines to form thioureido linkage between the compound of interest and the dye; succinimidyl esters such as NHS-fluorescein reactive towards amino groups to form an amido bond; maleimide active fluorophores such as fluorescein-5-maleimide which readily reactive with sulfhydryl groups. Following a fluorophore (or quencher) labeling reaction, it may be necessary to remove any unreacted fluorophore or quencher and this is often accomplished by size exclusion chromatography.

F. Particles

The particles may be made of biodegradable or non-biodegradable materials. For example, the particles may be made of polystyrene. Non-biodegradable particles may be provided with a removal means to prevent harmful buildup in the body. Generally, the particles may be designed to have a long half-life so that they remain in the vasculature or body fluids over several measurement periods. Depending on the lifetime of the particles, however, the user of the wearable device may periodically introduce new batches of antibody-particle conjugates into the vasculature or body fluids.

Nanoparticles have been the subject of considerable research interest, particularly in the fields of diagnostics and drug therapy. Nanoparticles are defined as particulate dispersions or solid particles with a size ranging from 10 to 1000 nm. Nanoparticles can be synthesized by a variety of methods including the sol-gel process, dispersion of pre-formed polymers, polymerization of monomers, ionic gelation or coacervation of hydrophilic polymers and can be prepared from a variety of materials include metals, proteins, polysaccharides, or synthetic polymers. The selection of materials can be dependent on many factors including (a) the size of the nanoparticles required; (b) desired surface characteristics such as charge and permeability; (c) degree of biodegradability, biocompatibility and toxicity; and (d) if the nanoparticle is used as a carrier to deliver a payload such as a drug, the inherent properties of the drug such as the aqueous solubility and stability.

Particle size and size distribution can be important characteristics of nanoparticle systems as they determine the in vivo distribution, biological fate, toxicity and the targeting ability of the nanoparticle systems. In addition, they can also influence the drug loading, drug release and stability of nanoparticles.

Nanoparticles can act as scaffolds for immobilization of detection elements such as antibodies, enhance electron transfer, catalyze electrochemical reactions or act as reactant themselves. Surface modification of nanoparticles can drastically improve biocompatibility, half-life and biodistribution. The conjugation of antibodys to nanoparticles allows for the detection and quantitation of target analytes or cell surfaces in vivo. The antibody-particle conjugates can act as a binding agent, a molecular switch or both, to measure the in vivo levels of target analytes such as biomolecules, ions and cells of interest. Two or more different antibodies may be used to improve avidity to a target analyte or to create particles that can detect multiple different target analytes. The binding or release of the antibody-nanoparticle conjugate to a target analyte in vivo can trigger a conformational change to cause a more stable confirmation that permits subsequent binding of a detectable agent such as a fluorophore, increase or decrease fluorescence via FRET, release/bind a secondary detectable molecule, or cause targeted release of a molecular payload such as a drug, ion or a sensor. For antibody-particle conjugates targeted to a receptor on a cell surface, a conformational change may occur which can increase or decrease fluorescence via FRET, lead to endocytosis followed by a pH change that leads to a detectable conformational change of the antibody or lead to endocytosis followed by a pH change in the endosome which may be detected by a pH sensitive dye.

Antibodies can be used in diagnostic procedures, or even in therapy to destroy a specific target, such as antitumor therapy or targeted chemotherapy. The particles can be designed to remove from the body or destroy the target analyte once bound to the antibody. Additional functional groups can be added to the particles to signal that the particles can be removed from the body through the kidneys, for example, once bound to the target analyte.

Further, the particles may be designed to either releasably or irreversibly bind to the target analyte. For example, if it is desired for the particles to participate in destruction or removal of the target analyte from the body, as described above, the particles may be designed to irreversibly bind to the target analyte. In other examples, the particles may be designed to release the target analyte after measurement has been made, either automatically or in response to an external or internal stimulus.

Antibody-particle conjugates can be used for detection and/or monitoring of target analytes in vivo. Representative examples of target analytes include, without limitation, serum glucose, calcium, blood urea nitrogen, creatinine, creatine kinase, sodium, potassium chloride, carbon dioxide, oxygen, serum calcium, serum total protein (TP), human serum albumin, bilirubin, alkaline phosphatase (ALP) aspartate amino transferase (AST), alanine amino transferase (ALT), glucose and insulin. Additional representative target analytes include lactate, cardiac enzymes, pharmaceuticals, hormones, cytokines, growth factors, circulating nucleic acids, circulating peptides, circulating viruses, and circulating cells.

The antibody-particle conjugates could also be used for in vivo enrichment and extraction of low abundance circulating biomarkers. For instance, the antibody-particle conjugates can be circulated and any biomolecules bound to the antibodies may be eluted off and analyzed in vitro.

Those of skill in the art will understand the term "particle" in its broadest sense and that it may take the form of any fabricated material, a molecule, cryptophan, a virus, a phage, etc. Further, a particle may be of any shape, for example, spheres, rods, non-symmetrical shapes, etc., and may be made of a solid, liquid or gaseous material or combinations thereof. The particles can have a diameter that is less than about 20 micrometers. In some embodiments, the particles have a diameter on the order of about 10 nanometers to 1 micrometer. In further embodiments, small particles on the order of 10-100 nanometers in diameter may be assembled to form a larger "clusters" or "assemblies on the order of 1-10 micrometers. In this arrangement, the assemblies would provide the signal strength of a larger particle, but would be deformable, thereby preventing blockages in smaller vessels and capillaries.

Binding of the antibody-particle conjugates to a target analyte may be detected with or without a stimulating signal input. The term "binding" is understood in its broadest sense to include any detectable interaction between the antibody and the target analyte. For example, some particles may be functionalized with compounds or molecules, such as fluorophores or autofluorescent, luminescent or chemiluminescent markers, which generate a responsive signal when the particles bind to the target analyte without the input of a stimulus. In other examples, the antibody-particle conjugates may produce a different responsive signal in their bound versus unbound state in response to an external stimulus, such as an electromagnetic, acoustic, optical, or mechanical energy.

Further, the particles may be formed from a paramagnetic or ferromagnetic material or be functionalized with a magnetic moiety. The magnetic properties of the particles can be exploited in magnetic resonance detection schemes to enhance detection sensitivity. In another example, an external magnet may be used to locally collect the particles in an area of subsurface vasculature during a measurement period. Such collection may not only increase the differential velocity between particles and analytes, hence surveying a much larger volume per unit time, but may also enhance the signal for subsequent detection.

Suitable particles including nanoparticles can be prepared by any suitable means. See, for instance, Y. Deng et al., *J. Magnetism and Magnetic Materials*, Vol. 257, pp. 69-78 (February 2003) and W. Fang et al., *J. Mater. Chem*, 2010, Vol. 20, pp. 8624-8630 DOI: 10.1039/C0JM02081H, both describing preparation of polymeric magnetic particles, which references are incorporated by reference in their entirety. Suitable particles including magnetic microparticles and nanoparticles are also available commercially. See, for instance, Chemicell GmBH, Berlin, Germany; and Ademtech Inc., New York, N.Y., USA.

G. Preparation of Detection Probes

Antibody-particle conjugates can be prepared by any suitable means. For instance, antibodies have been developed that are specific for target analytes including cell types. See, for instance, Harlow, E., and Land, D. in "Antibodies: A Laboratory Manual," Cold Spring Harbor Press (New York, 1988); Siddiqui MZ, "Monoclonal Antibodies as Diagnostics; an Appraisal," Indian J. Pharm. Sci., January 2010, Vol. 72(1):12-17, doi:10.4103/0250-474X.62229; and Borrebaeck, C. A. K. (2000), "Antibodies in diagnostics—from Immunoassays to Protein Chips," Immunology Today, Vol. 21(8):379-382. In one embodiment, antibodies can be conjugated first to the nanoparticles and the nanoparticle conjugated antibodies are then subsequently labeled with a fluorophore. In another embodiment, the antibodies are first labeled with a fluorophore and the labelled antibodies are then conjugated to the nanoparticles. Quencher-labeled protein M is then complexed to the nanoparticle-labeled antibody conjugate to form the detection probe. In another embodiment, a complex of fluorophore-labeled antibody and quencher-labeled protein M is conjugated to the particle by any suitable method. Representative methods are described for instance at Arruebo et al. J. Nanomaterials, 2000, Vol. 2009, Article ID 439389 (http://dx.doi.org/10.1155/2009/439389).

V. Illustrative Methods for Detecting One or More Target Analytes

A method for a homogeneous competitive displacement FRET method is provided for detection of target analytes by direct binding and detection in one step without the need for wash steps. The method can be used in vivo or in vitro to detect for the presence of one or more target analytes in solution, e.g., bodily fluid such as blood or perspiration. The method employs a composition as a detection probe which includes a particle conjugated to complex of a fluorophore labeled-antibody and quencher labeled-protein M which binds to a human antibody binding site and competes non-specifically for access to the antibody combining site.

In one embodiment, the method employs a detection probe which includes a particle, e.g., nanoparticle, that is conjugated to a complex of a fluorophore-labeled antibody 1420 and quencher-labeled protein M (Mq) as previously described. As defined herein, a "fluorophore" is a molecule (e.g., colored dye) which emits light at a specific range of wavelengths or segment of the spectrum after excitation by light of a lower wavelength or lower range of wavelengths versus the emission wavelengths. Different types of fluorophores emit energy at different wavelengths or spectral ranges. As defined herein, a "quencher" is a molecule which absorbs light energy (or photons) at a specific spectral range of wavelengths and does not re-emit light, but converts virtually all of the excitation light energy into invisible vibrations (e.g., infrared or heat). Different types of quenchers absorb energy at different wavelengths or spectral ranges. By placing the fluorophore of the antibody and quencher of protein at a suitable proximity between each other, the fluorophore can be "quenched" by the quencher.

Figure 14:
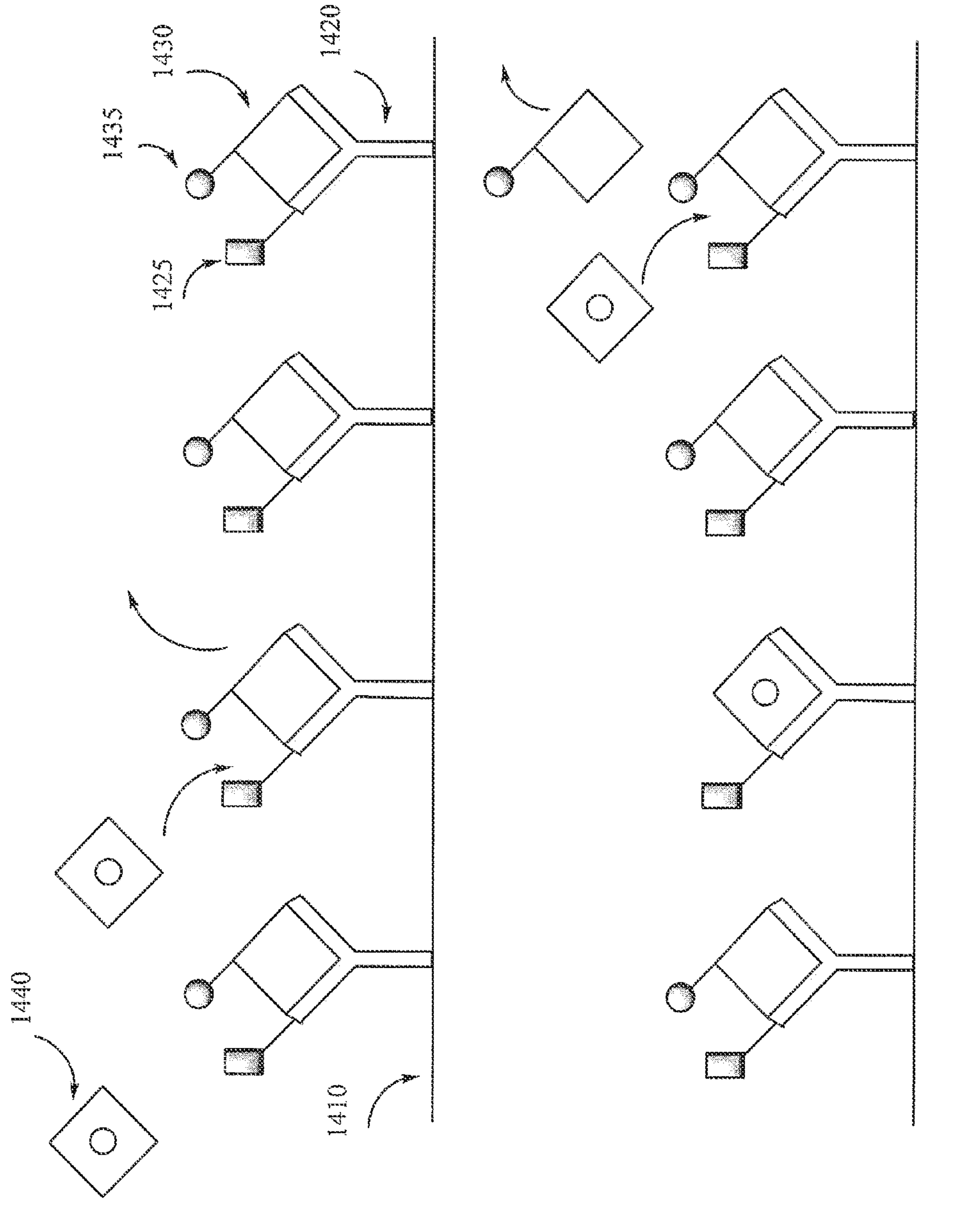
FIG. 14 illustrates a representative method.

FIG. 14 shows a method for the detection of a target analyte of interest is done by means of FRET. Detection probes including an antibody 1420 labeled with a fluorophore 1425 are conjugated to the surface of a particle 1410 as described previously are attached to the surface of a particle. The binding site of the immobilized antibody 1420 is complexed with Mq 1430 (protein M conjugated to a quencher 1435) prior to exposure to target analytes 1440. When target analyte 1440 is present, it competes for the specific binding sites on antibody 1420, displacing a portion of the Mq 1430 into the solution. The degree of displacement of Mq 1430 depends upon the concentration of the target analyte 1440 in the solution. Therefore, measurement of the amount of fluorescence generated after displacement of Mq 1430 and photoexcitation of the fluorophore label, when suitably calibrated, provides a quantitative measure of the concentration of target analyte 1440.

Figure 15:
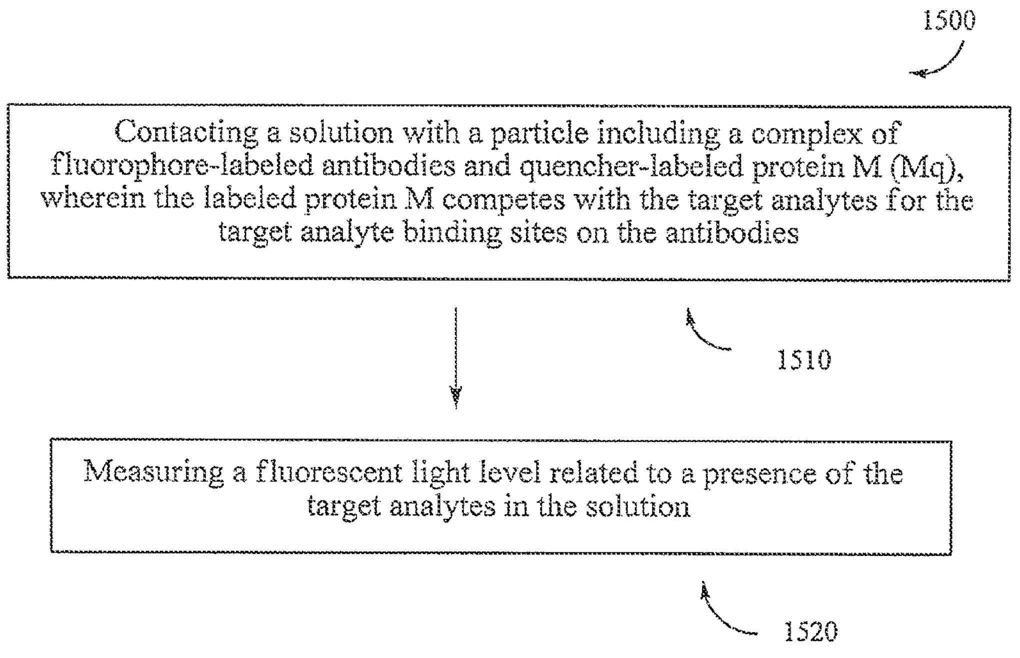
FIG. 15 illustrates a flowchart of a representative method.

The method provided using nanoparticles coupled with labeled antibody-Mq is useful for detecting specific target analytes by competitive FRET in vivo. It has been determined that nanoparticles coupled with a complex of a fluorophore-labeled antibody and quencher-labeled protein M (Mq) are useful in a homogeneous competitive FRET-based assay to enable detection of one or more target analytes in a solution. When target analyte is present at a certain concentration in solution either in vivo or in vitro, the target analyte competes with and displaces Mq from the complex, resulting in fluorescent emission from the fluorophore following photoexcitation with an interrogating signal and thereby providing a mechanism for detecting and quantitating target analytes in a solution, e.g., bodily fluid. As shown in FIG. 15, the method 1500 includes (i) contacting a solution with a particle including a complex of fluorophore-labeled antibodies and quencher-labeled protein M (Mq), wherein the labeled protein M competes with the target analytes for the target analyte binding sites on the antibodies 1510, wherein the fluorophore and quencher are specially matched such that there is a detectable change in the fluorescent signal of the labeled antibodies when the fluorophore and the quencher are moved into or out of functional proximity, wherein fluorescent light levels change proportionately in response to the amount of target analytes that are able to bind with the labeled antibodies; and wherein the solution may include one or more target analytes, and (ii) measuring a fluorescent light level related to a presence of the target analytes in the solution 1520.

Figure 16:
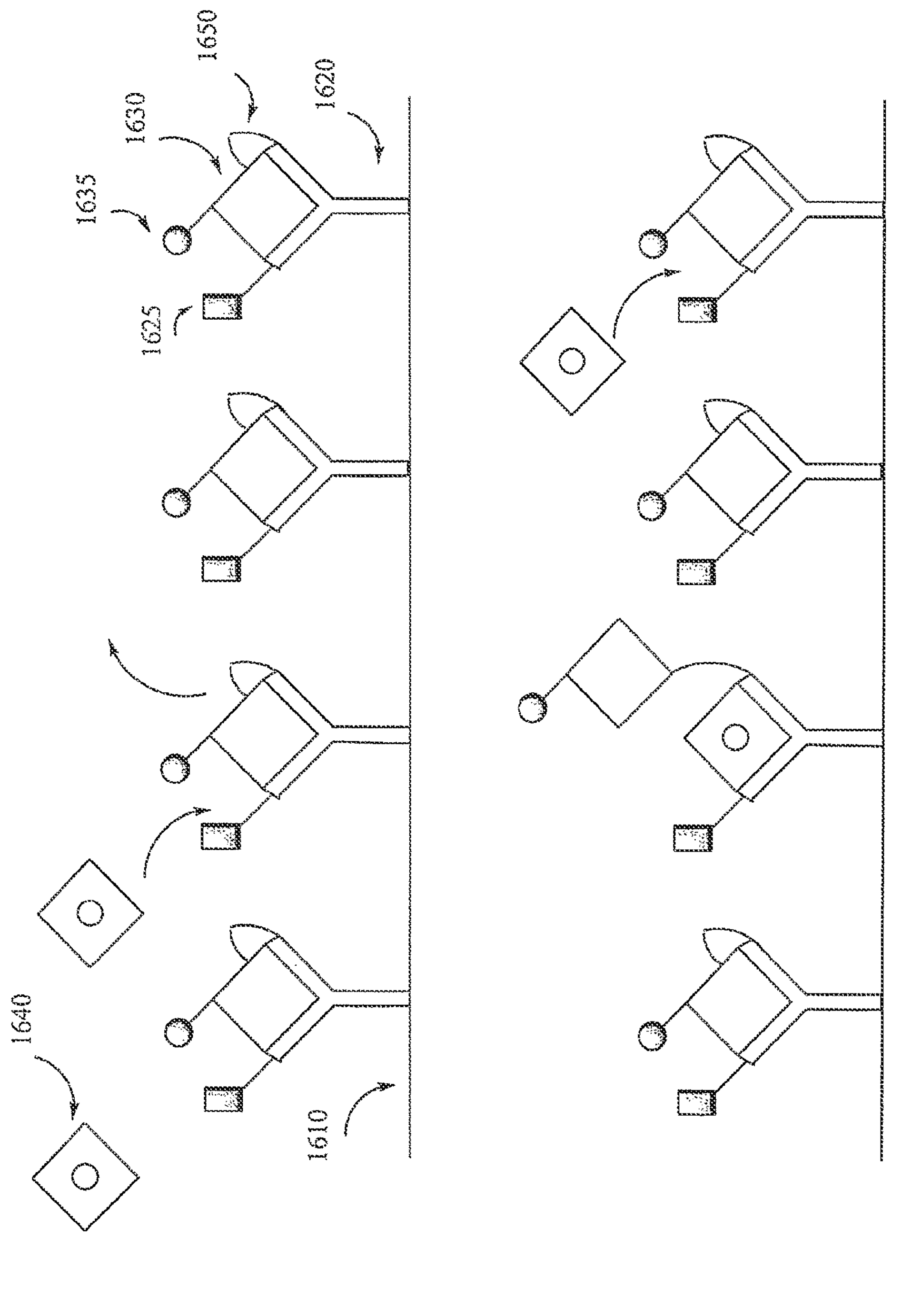
FIG. 16 illustrates a representative method.
Figure 17:
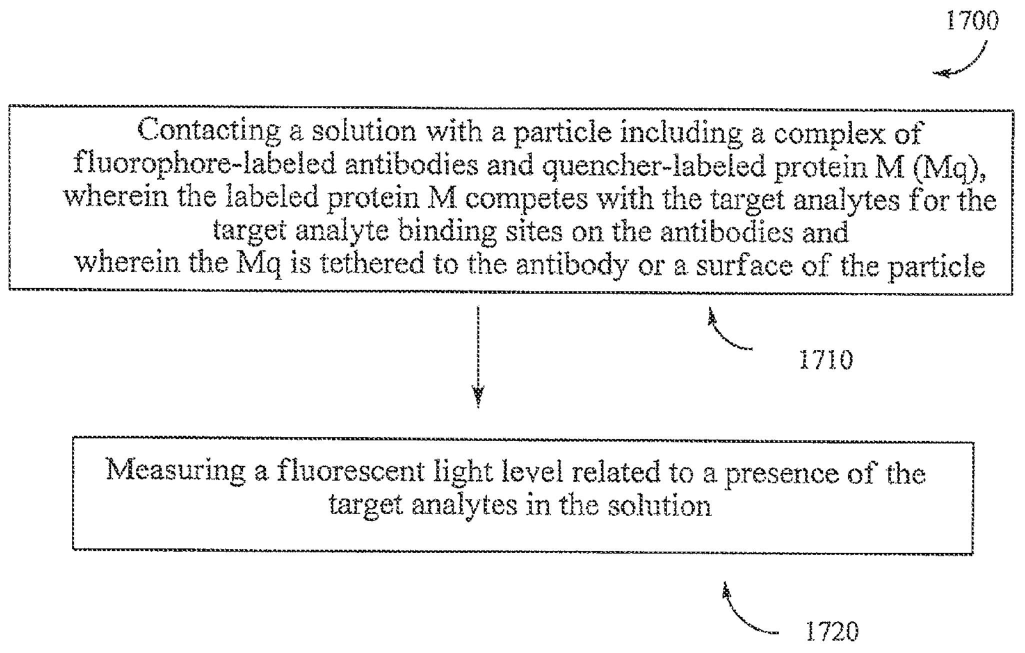
FIG. 17 illustrates a flowchart of a representative method.

In one embodiment, a competitive method is provided whereby the displacement of Mq by the target analyte is irreversible. In another embodiment, a reversible competitive method is provided whereby the displacement of Mq is reversible. In this embodiment as shown in FIG. 16, protein M 1630 can be engineered with a sufficiently low affinity and is covalently tethered via a linker 1650 of a suitable length to the antibody. Alternatively, protein M can be covalently tethered via a linker to the surface of the nanoparticle (not shown). Either arrangement, Mq 1630 can be competitively displaced off the antibody combining site on the antibody 1620 in the presence of the target analyte 1640 at a certain concentration in vivo but the tether 1650 prevents the quencher-labeled protein M 1630 from diffusing away. Upon suitable change in assay conditions, the quencher-labeled protein M 1630 in the detection probe can displace the target analyte 1640, recharging the detection probe for future use. Thus, as shown in FIG. 17, the method 1700 includes (i) contacting a solution with a particle including a complex of fluorophore-labeled antibodies and quencher-labeled protein M (Mq), wherein the labeled protein M competes with the target analytes for the target analyte binding sites on the antibodies 1710, wherein the fluorophore and quencher are specially matched such that there is a detectable change in the fluorescent signal of the labeled antibodies when the fluorophore and the quencher are moved into or out of functional proximity, wherein fluorescent light levels change proportionately in response to the amount of target analytes that are able to bind with the labeled antibodies; and wherein the solution may include one or more target analytes, and wherein the Mq is tethered to the antibody or a surface of the particle; and (ii) measuring a fluorescent light level related to a presence of the target analytes in the solution 1720.

In another embodiment, multiple analyte detection is possible. By immobilizing a plurality of antibodies of different binding specificity to target analytes, each antibody bound to Mq and labeled with a distinct fluorophore-quencher pair with distinct emission and excitation spectra, multiple target analyte determinations can preferably be made. The use of spectral filters and/or alternative light sources as the interrogation signal can be used to photoexcite the fluorophores and detect fluorescent light from the different fluorophores, and thereby, determine the contribution of each fluorophore to the total fluorescent properties of the sample.

V. Illustrative Methods for Operation of a Wearable Device

Figure 18:
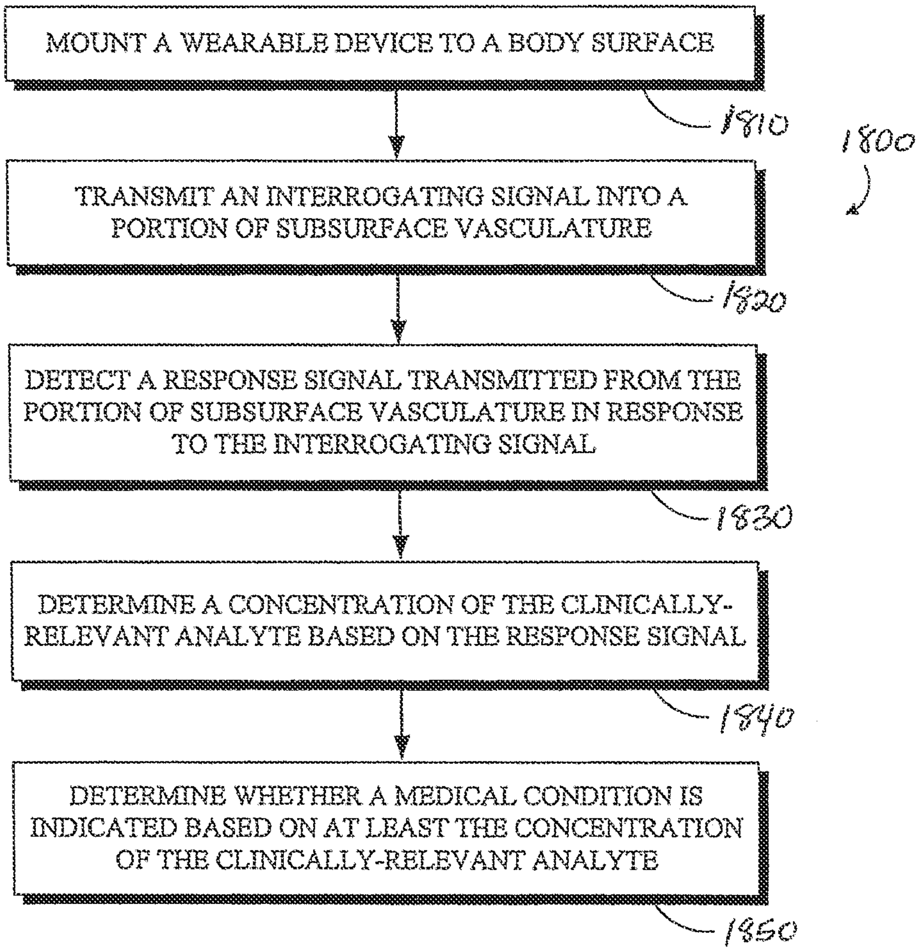
FIG. 18 is a flowchart of an example method for operating a wearable device.

FIG. 18 is a flowchart of a method 1800 for operating a wearable device to take non-invasive, in vivo, real-time measurements of physiological parameters. A wearable device is first mounted to a body surface of a human subject, wherein the body surface is proximate to a portion of subsurface vasculature (1810). In some examples, the wearable device, via a signal source, transmits an interrogating signal into the portion of subsurface vasculature (1820). The wearable device, via a detector, then detects a response signal transmitted from the portion of subsurface vasculature, wherein the response signal is related to binding of a clinically-relevant analyte to antibody conjugates, e.g., antibody-particle conjugates, present in a lumen of the subsurface vasculature (1830). In some examples, the response signal is generated in response to an interrogating signal. The antibody conjugates, e.g., antibody-particle conjugates, are configured to bind to the clinically-relevant analyte and comprise one or more types of antibody. The term "bind" is understood in its broadest sense to also include any detectable interaction between the clinically relevant analyte and the antibody conjugates, e.g., antibody-particle conjugates. The wearable device then determines the presence, absence and/or a concentration of the clinically-relevant analyte based on the response signal (1840) and whether a medical condition is indicated based on at least the presence, absence and/or concentration of the clinically-relevant analyte (1850). Further, in examples where the antibody conjugates, e.g., antibody-particle conjugates, are magnetic, the wearable device may further direct a magnetic field into the portion of subsurface vasculature, the magnetic field being sufficient to cause the antibody—magnetic particle conjugates to collect in a lumen of the portion of subsurface vasculature.

Figure 19A:
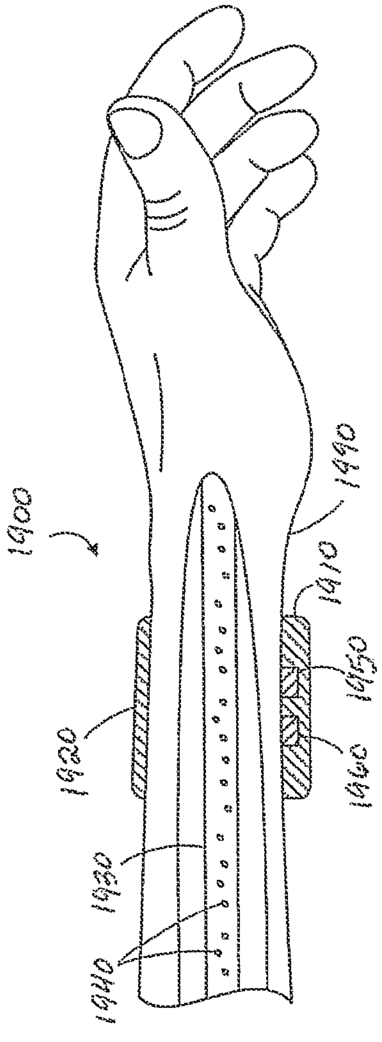
FIG. 19A is side partial cross-sectional view of an example wrist-mounted device, while on a human wrist.
Figure 19B:
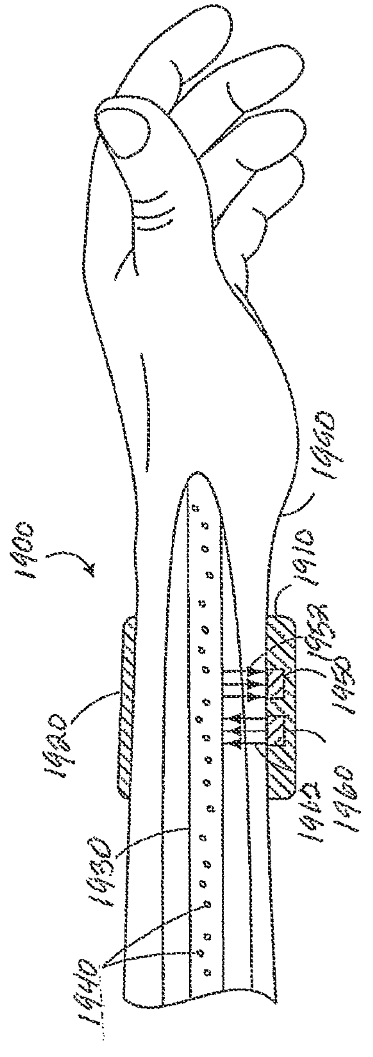
FIG. 19B is side partial cross-sectional view of an example wrist-mounted device, while on a human wrist.

FIGS. 19A-19B, 20A-20B, and 21A-21B are partial cross-sectional side views of a human wrist illustrating the operation of various examples of a wrist-mounted device. In the example shown in FIGS. 19A and 19B, the wrist-mounted device 1900 includes a measurement platform 1910 mounted on a strap or wrist-band 1920 and oriented on the anterior side 1990 of the wearer's wrist. Measurement platform 1910 is positioned over a portion of the wrist where subsurface vasculature 1930 is easily observable. Antibody-particle conjugates 1940 have been introduced into a lumen of the subsurface vasculature by one of the means discussed above. In this example, measurement platform 1910 includes a data collection system having both a detector 1950 and a signal source 1960. FIG. 19A illustrates the state of the subsurface vasculature when measurement device 1900 is inactive. The state of the subsurface vasculature during a measurement period is illustrated in FIG. 19B. At this time, signal source 1960 is transmitting an interrogating signal 1962 into the portion of subsurface vasculature and detector 1950 is receiving a response signal 1952 generated in response to the interrogating signal 1962. The response signal 1952 is related to the binding of a clinically relevant analyte present in the subsurface vasculature to the antibody-particle conjugates 1940. As described above, in some embodiments, an interrogating signal may not be necessary to generate a response signal related to the binding of an analyte to the antibody-particle conjugates if the label on the antibody is autofluorescent or luminescent for instance.

Figure 20A:
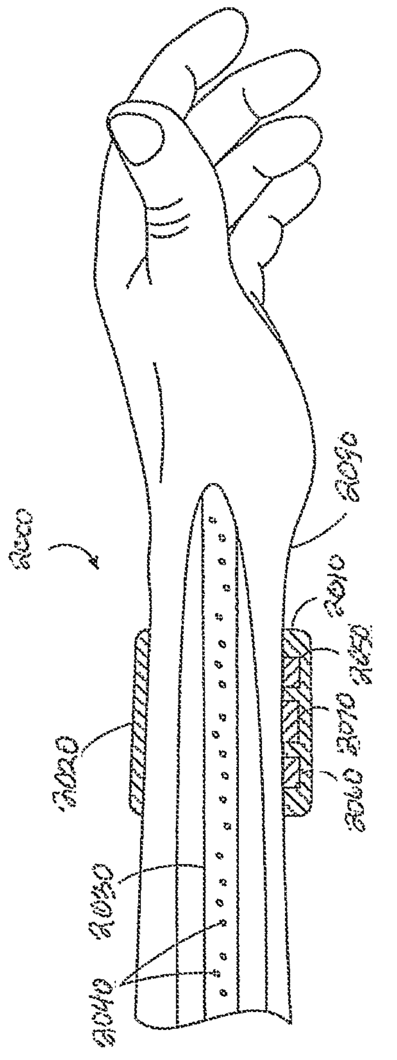
FIG. 20A is side partial cross-sectional view of an example wrist-mounted device, while on a human wrist.
Figure 20B:
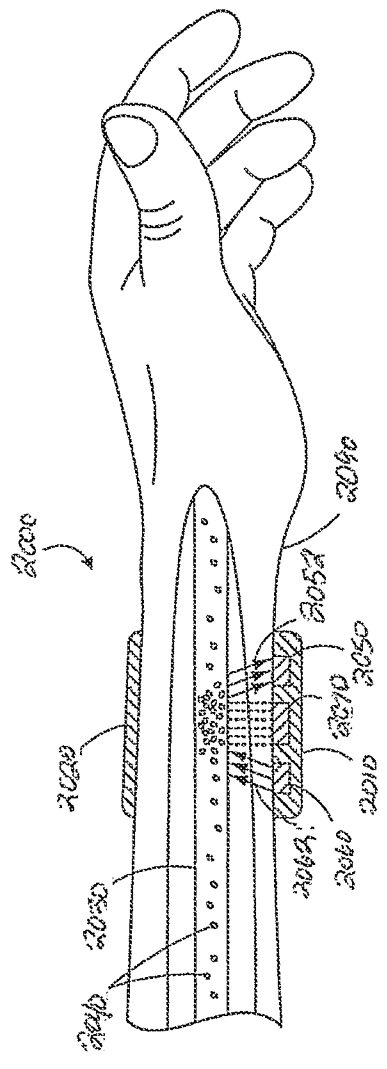
FIG. 20B is side partial cross-sectional view of an example wrist-mounted device, while on a human wrist.

Similar to the system depicted in FIGS. 19A and 19B, FIGS. 20A and 20B illustrate a wrist-mounted device 2000 including a measurement platform 2010 mounted on a strap or wristband 2020 and oriented on the anterior side 2090 of the wearer's wrist. In this example, measurement platform 2010 includes a data collection system having a detector 2050, a signal source 2060 and a collection magnet 2070. FIG. 20A illustrates the state of the subsurface vasculature when measurement device 2000 is inactive. The state of the subsurface vasculature when measurement device 2000 is active during a measurement period is illustrated in FIG. 20B. At this time, collection magnet 2070 generates a magnetic field 2072 sufficient to cause antibody-magnetic particle conjugates 2040 present in a lumen of the subsurface vasculature 2030 to collection in a region proximal to the magnet 2070. Signal source 2060 transmits an interrogating signal 2062 into the portion of subsurface vasculature and detector 2050 is receiving a response signal 2052 generated in response to the interrogating signal 2062. The response signal 2052 is related to the binding of a clinically relevant analyte present in the subsurface vasculature to the antibody-magnetic particle conjugates 2040. As described above, in some embodiments, an interrogating signal may not be necessary to generate a response signal related to the binding of an analyte to the antibody-magnetic particle conjugates.

Figure 21A:
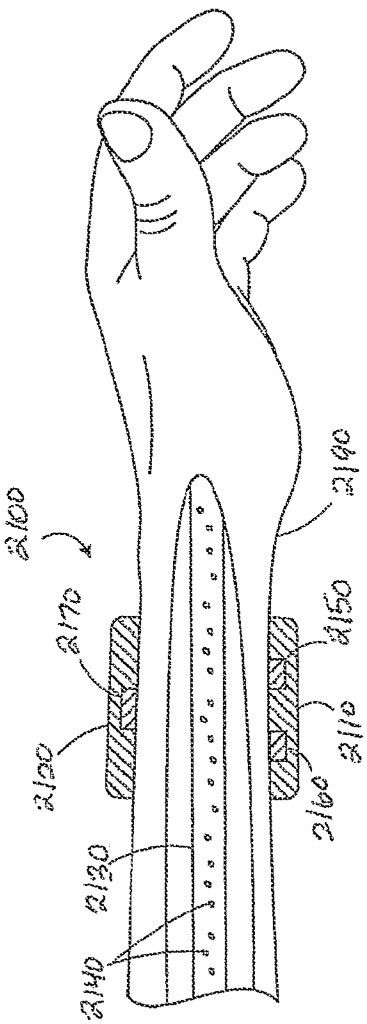
FIG. 21A is side partial cross-sectional view of an example wrist-mounted device, while on a human wrist.
Figure 21B:
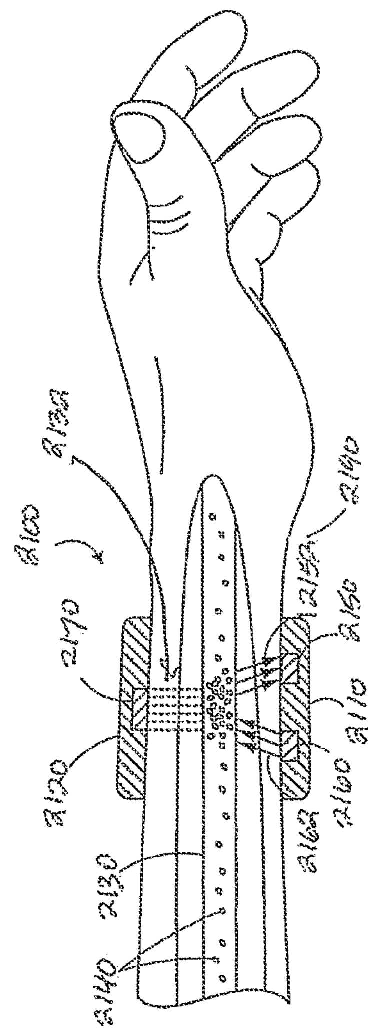
FIG. 21B is side partial cross-sectional view of an example wrist-mounted device, while on a human wrist.

FIGS. 21A and 21B illustrate a further embodiment of a wrist-mounted device 2100 having a measurement platform 2110 disposed on a strap 2120, wherein the detector 2150 and signal source 2160 are positioned on the posterior side 2190 of the wearer's wrist and the collection magnet 2170 is disposed on the anterior side 2180 of the wearer's wrist. Similar to the embodiments discussed above, FIG. 21A illustrates the state of the subsurface vasculature when measurement device 2100 is inactive. The state of the subsurface vasculature when measurement device 2100 is active during a measurement period is illustrated in FIG. 21B. At this time, collection magnet 2170 generates a magnetic field 2132 sufficient to cause antibody-magnetic particle conjugates 2140 present in a lumen of the subsurface vasculature 2130 to collection in a region proximal to the magnet 2170. Signal source 2160 transmits an interrogating signal 2162 into the portion of subsurface vasculature and detector 2150 is receiving a response signal 2152 generated in response to the interrogating signal 2162. The response signal 2152 is related to the binding of a clinically relevant analyte present in the subsurface vasculature to the antibody-magnetic particle conjugates 2140. As described above, in some embodiments, an interrogating signal may not be necessary to generate a response signal related to the binding of an analyte to the antibody-magnetic particle conjugates.

Both FIGS. 20B and 21B illustrate the path of the interrogating signal (2062, 2162) transmitted by the signal source (2060, 2160) and the responsive signal (2052, 2152) detected by the detector (2050, 2150) essentially overlapping over a portion of subsurface vasculature. In some examples, the signal source (2060, 2160) and the detector (2050, 2150) may be angled towards each other so that they are interrogating and detecting from essentially the same area of subsurface vasculature. However, in some instances, such as in the example shown in FIG. 19B, the paths of the interrogating signal (2062, 2162) transmitted by the signal source (2060, 2160) and the responsive signal (2052, 2152) detected by the detector (2050, 2150) may not overlap.

Figure 22:
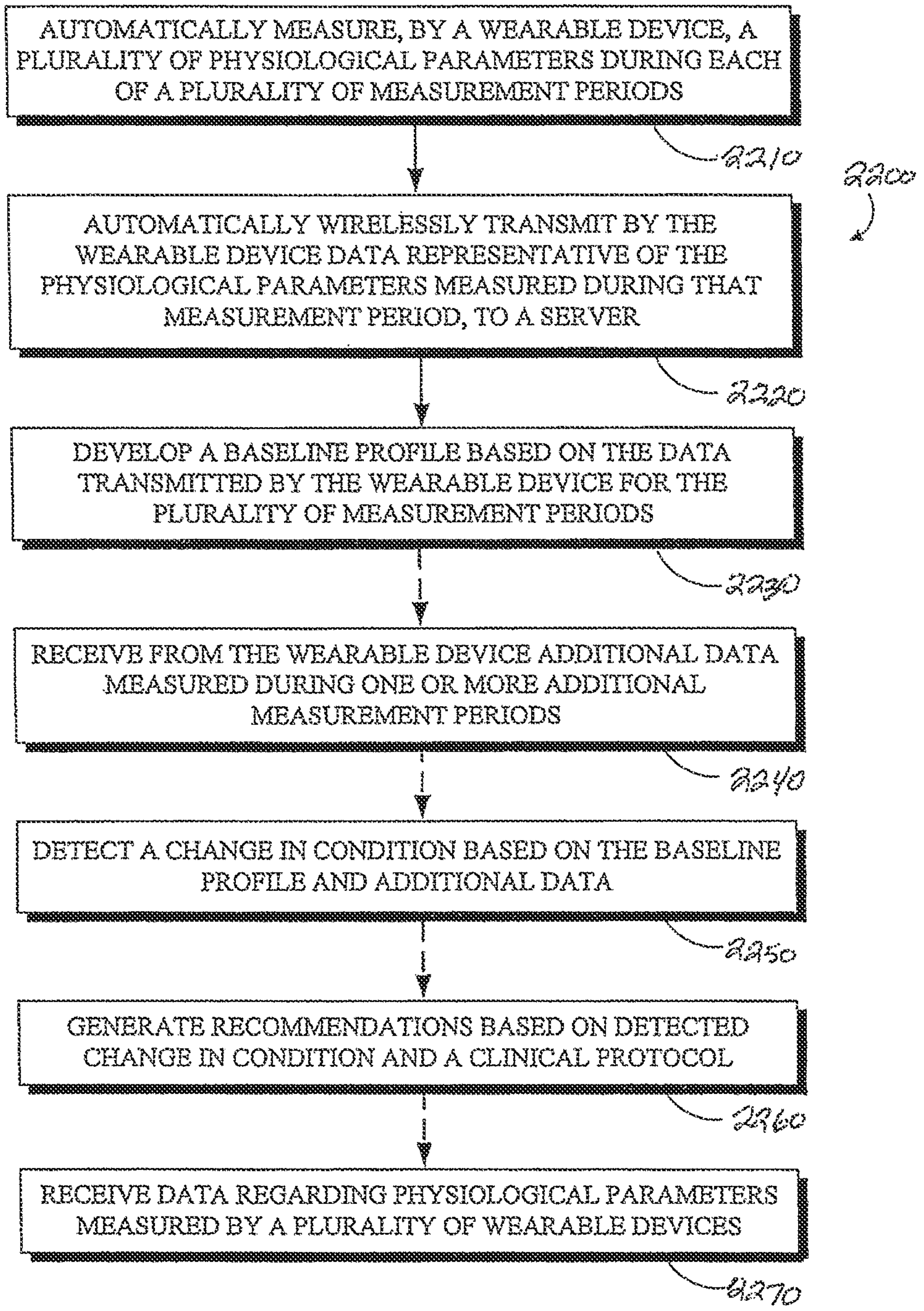
FIG. 22 is a flowchart of an example method for using a wearable device to take real-time, high-density, non-invasive, in vivo measurements of physiological parameters.

VI. Illustrative Methods for Real-Time, High-Density Physiological Data Collection Using a Wrist Mounted Device FIG. 22 is a flowchart of a method 2200 for using a wearable device to take real-time, high-density, non-invasive, in vivo measurements of physiological parameters. In a first step, the wearable device automatically measures one or more physiological parameters during each of a plurality of measurement periods (2210). The length of the measurement period may be set on the device itself or may be set remotely, for example, by instruction from a remote server. The device may be configured with many measurement periods each day—for example, continuous, every second, every minute, every hour, every 6 hours, etc.—or may be configured to take measurements once a week or once a month. Further, a different measurement period may be set for each of the physiological parameters being measured. The measurement periods may extend through a plurality of consecutive days and each of the consecutive days may include multiple measurement periods. Each of the consecutive days may further include at least twenty-four measurement periods and the plurality of consecutive days may include at least thirty days. At least some of the physiological parameters are measured by non-invasively detecting one or more analytes in blood circulating in subsurface vasculature proximate to the wearable device.

After conclusion of a measurement period, for each of the plurality of measurement periods, the wearable device transmits to a server data representative of the physiological parameters measured during that measurement period (2220). The wearable device may be configured to automatically transmit the data to a server, may be configured to transmit on command of the wearer, or may be configured to transmit on instruction from a remote server. Further, the device may be configured to automatically transmit the data at the end of each measurement period, or at some more frequent or infrequent rate. For example, the device could be configured to transmit every five minutes, at the end of each day, at the end of the month, at nighttime only, etc.

In response, the server is configured to develop a baseline profile based on the data transmitted by the wearable device for the plurality of measurement periods (2230). In some embodiments, the baseline profile includes an individual baseline profile based on the data transmitted by the wearable device for the plurality of measurement periods for an individual user wearing the wearable device. As described above, the baseline profile may include patterns for how one or more of the wearer's physiological parameters typically change over time, such as during the course of a day, a week, or a month. The baseline profile may further include threshold values of certain target analytes, above or below which a medical condition may be indicated.

After the server has developed an individual baseline profile for a wearer of the device, the server may receive additional data regarding the physiological parameters from the wearable device measured during one or more additional measurement periods (2240). The server may then compare the additional data, collected over additional measurement periods, to the individual baseline profile. If the additional data is consistent with the patterns embodied in the individual baseline profile, the server may determine that the wearer's condition has not changed. On the other hand, if the additional data deviates from the patterns embodied in the baseline profile, the server may detect a change in the wearer's condition (2250). The change in condition could, for example, indicate that the wearer has developed a disease, disorder, or other adverse medical condition or may be at risk for a severe medical condition, such as a stroke or a heart attack, in the near future.

If the server detects a change in condition based on the individual baseline profile and the additional data, it may generate one or more recommendations based on the detected change in condition and a clinical protocol (2260). For example, the server may generate a recommendation that the wearer take a particular medication or supplement, schedule an appointment with a medical professional, go to the hospital to seek immediate medical attention, abstain from certain activities, etc. The server may also be configured to receive data regarding physiological parameters measured by a plurality of wearable devices (2270) and use that data to develop, at least in part, the clinical protocol. The clinical protocol may also be developed based, at least in part, on any known health information or medical history of the wearer, and/or on recognized standards of care in the medical field. The wearable device may receive the one or more recommendations generated by the server (2270) and provide an indication of the one or more recommendations via a user interface on the wearable device.

In some embodiments, the server may be configured to receive data regarding physiological parameters measured by a plurality of wearable devices. The server may use this data collected from a plurality of wearable devices—worn by a plurality of users—to develop, at least in part, a population baseline profile. Such population baseline profiles may be used, for example, for comparison with an individual's baseline profile. Those of skill in the art will readily recognize that comparison of an individual's physiological parameters measured over time to that individual's own baseline may not be sufficient to recognize an abnormality in that physiological parameter. For example, while a physiological parameter for an individual wearer of the device may not deviate from that individual's baseline, that individual baseline may be well above the population baseline generated from data collected from a plurality of wearers of the device. Thus, comparison to what is "normal" or "average" for a population may be necessary for effective identification or prevention of a medical condition in an individual.

Accordingly, the server may further be configured to receive from the wearable device additional data measured during one or more additional measurement periods, detect a change in condition based on the population baseline profile and the additional data, and generate one or more recommendations based on the detected change in condition and a clinical protocol. The wearable device may receive the one or more recommendations generated by the server and provide an indication of the one or more recommendations via a user interface on the wearable device.

Figure 23:
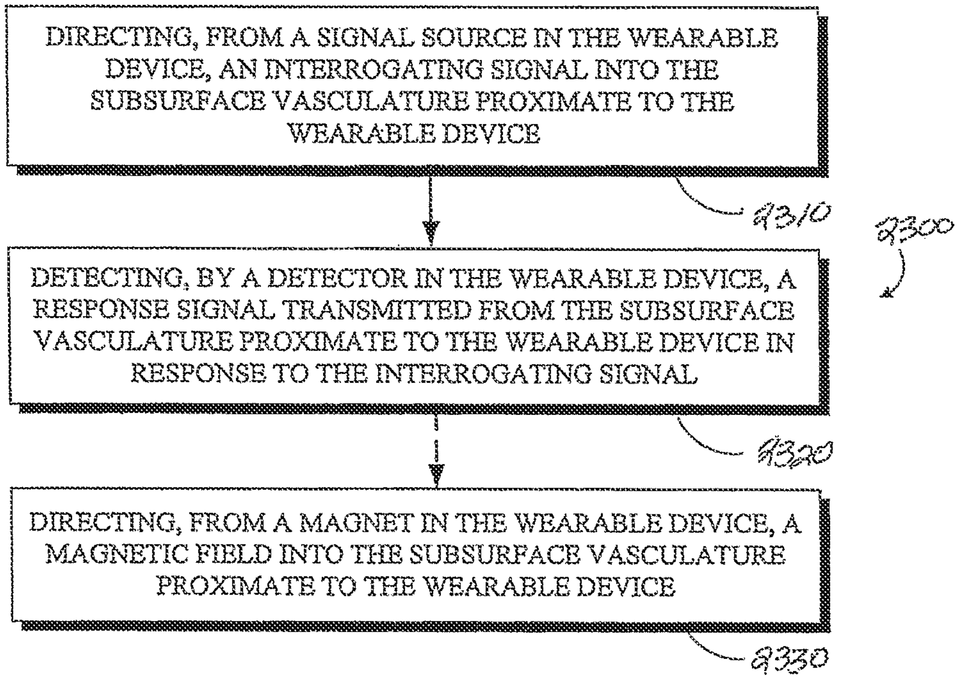
FIG. 23 is a flowchart of an example method for using a wearable device to take real-time, high-density, non-invasive, in vivo measurements of physiological parameters, in particular steps for measuring one or more analytes in blood circulating in subsurface vasculature proximate to the wearable device.

In further embodiments, the method may include introducing antibody-particle conjugates into the blood, wherein the antibody-magnetic particle conjugates are configured to bind to the one or more analytes. As shown in FIG. 23, the wearable device may non-invasively measure one or more analytes in blood circulating in subsurface vasculature proximate to the wearable device by directing, from a signal source in the wearable device, an interrogating signal into the subsurface vasculature proximate to the wearable device (2310). As discussed above, this step may not be necessary in cases where the antibody-particle conjugates generate a response signal related to binding of the one or more analytes without the need for an interrogating signal. In any case, the wearable device may detect, with a detector, a response signal transmitted from the subsurface vasculature proximate to the wearable device in response to the interrogating signal (2320). The response signal is related to binding of the one or more analytes to the antibody-particle conjugates. In examples where an interrogating signal is used, the interrogating signal may include a time-varying magnetic field and the response signal may include an externally-detectable physical motion due to the time-varying magnetic field. The interrogating signal may include an electromagnetic pulse (e.g., a radio frequency (RF) pulse) and the response signal may include a magnetic resonance (MR) signal. The interrogating signal may include electromagnetic radiation having a wavelength between about 400 nanometers and about 1600 nanometers, more particularly, a wavelength between about 500 nanometers and about 1000 nanometers. Where the antibody-particle conjugates also include a fluorophore, the response signal may include fluorescence radiation transmitted by the fluorophore in response to the interrogating signal.

In some examples, the antibody-particle conjugates may also be magnetic. The process of measuring one or more analytes in blood circulating in subsurface vasculature may further include directing, from a magnet in the wearable device, a magnetic field into the subsurface vasculature proximate to the wearable device (2330). The magnetic field is sufficient to cause the antibody-magnetic particle conjugates to collect in a lumen of the subsurface vasculature proximate to the wearable device.

Figure 24:
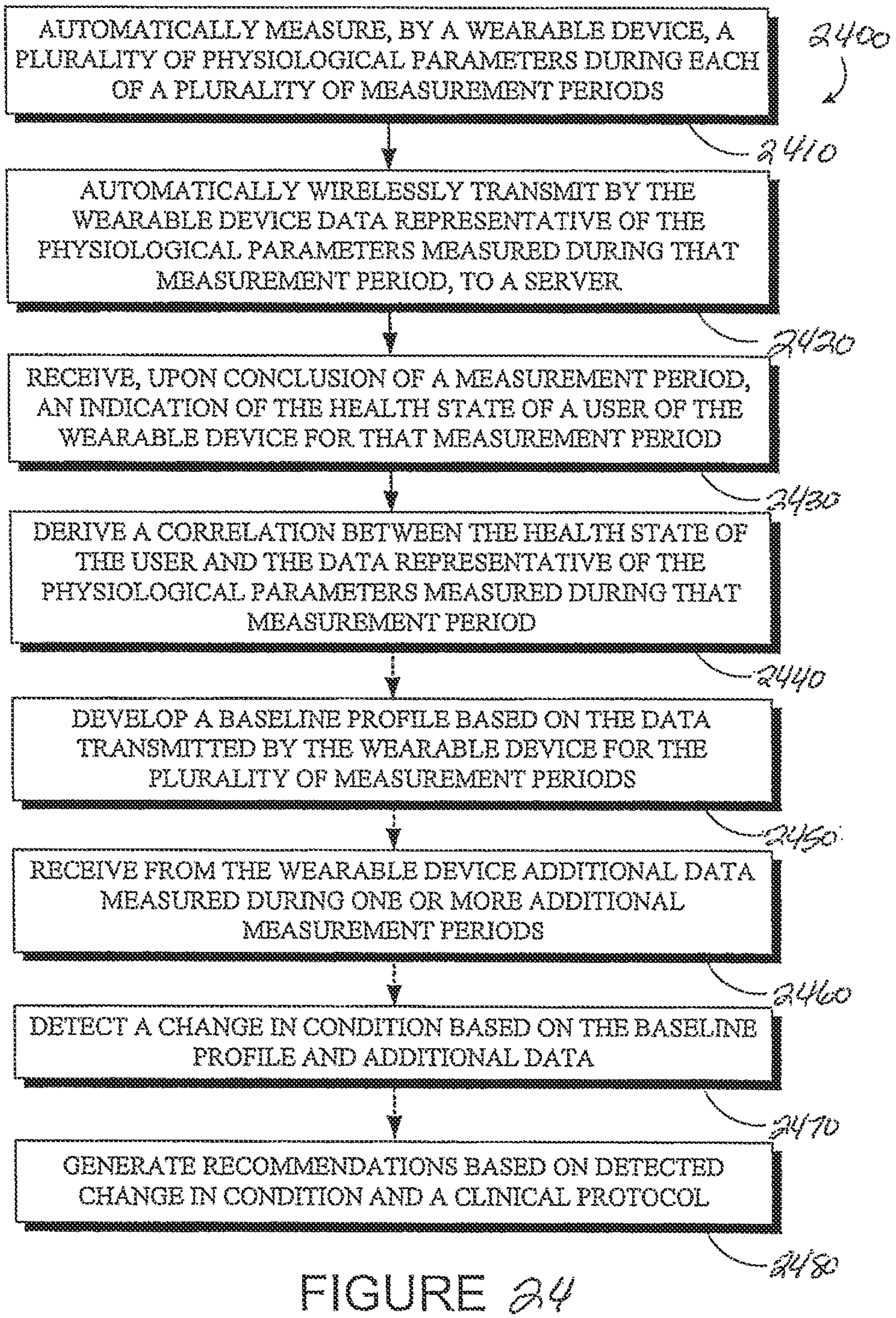
FIG. 24 is a flowchart of an example method for using a wearable device to take real-time, high-density, non-invasive, in vivo measurements of physiological parameters.

FIG. 24 is a flowchart of a method 2400 for using a wearable device to take real-time, high-density, non-invasive, in vivo measurements of physiological parameters. In a first step, the wearable device automatically measures one or more physiological parameters during each of a plurality of measurement periods (2410). The measurement periods may extend through a plurality of consecutive days, wherein each of the consecutive days includes multiple measurement periods. At least some of the physiological parameters are measured by non-invasively detecting one or more analytes in blood circulating in subsurface vasculature proximate to the wearable device.

Upon conclusion of a measurement period for each of the plurality of measurement periods, the wearable device automatically wirelessly transmits to a server data representative of the physiological parameters measured during that measurement period (2420). The server may be configured to receive, upon conclusion of a measurement period, an indication of the health state of a user of the wearable device for that measurement period (2430) and derive a correlation between the health state of the user and the data representative of the physiological parameters measured during that measurement period (2440). For example, the server may be configured to recognize patterns, for example, every time a physiological parameter reaches or drops to a certain level, the wearer of the device indicates that he or she experiences a migraine. Recognition of these patterns or correlations may help medical professionals to recognize, prevent, diagnose and/or treat of health conditions in that individual. Further, the server may be configured to use these correlations to alert the user that a medical condition may be imminent.

A baseline profile may be developed by the server based on the data transmitted by the wearable device for the plurality of measurement periods (2450). The server may further be configured to receive from the wearable device additional data representative of the physiological parameters measured during one or more additional measurement periods (2460), detect a change in condition based on the baseline profile and the additional data (2470), and generate one or more recommendations based on the detected change in condition and a clinical protocol (2480). The clinical protocol may be developed based, at least in part, on the derived correlation. For example, the clinical protocol may indicate that a medical condition may be imminent based on a comparison between current measurement of a physiological parameter and the derived correlation between previously measured physiological parameters and previously reported health state.

In a further example, the server may be configured to receive data regarding physiological parameters measured by a plurality of wearable devices and receive an indication of the health state of the users of the plurality of wearable devices for a plurality of measurement periods. The server may then derive a correlation between the health state of the users and the data representative of the physiological parameters measured during the plurality of measurement periods. Population data of this kind may be significant in that such correlations may never before have been drawn between that physiological parameter and a particular health condition. Such correlations may be used in prediction, prevention, diagnoses and treatment of health conditions. The server may also be configured to receive from the wearable device additional data representative of the physiological parameters measured during one or more additional measurement periods and generate one or more recommendations based on the received additional data and a clinical protocol, wherein the clinical protocol is developed based, at least in part, on the derived correlation.

In a further example, the wearable device itself may be configured to perform the steps described above as being performed by a remote server. For example, the wearable device may be configured to analyze the data representative of the physiological parameters, generate a baseline profile, compare data collected from additional measurement periods to the baseline profile, and generate recommendations based on a clinical protocol. The wearable device may further be configured to transmit, either automatically or on some other frequency, certain data to the remote server.

VII. Conclusion

Where example embodiments involve information related to a person or a device of a person, some embodiments may include privacy controls. Such privacy controls may include, at least, anonymization of device identifiers, transparency and user controls, including functionality that would enable users to modify or delete information relating to the user's use of a product.

Further, in situations in where embodiments discussed herein collect personal information about users, or may make use of personal information, the users may be provided with an opportunity to control whether programs or features collect user information (e.g., information about a user's medical history, social network, social actions or activities, profession, a user's preferences, or a user's current location), or to control whether and/or how to receive content from the content server that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims.

The invention claimed is:

1. A composition comprising:

a particle conjugated to a complex comprising (i) antibodies labeled with a fluorophore, the labeled antibodies having target analyte binding sites; and (ii) protein M labeled with a quencher that is complimentary to the fluorophore of the labeled antibodies, wherein the labeled protein M competes with target analytes for the target analyte binding sites on the labeled antibodies;

wherein the fluorophore and quencher are spectrally matched such that there is a detectable change in the fluorescent signal of the labeled antibodies when the fluorophore and the quencher are moved into or out of proximity to each other, and wherein fluorescent light levels change proportionately in response to the amount of target analytes that are able to bind with the labeled antibodies.

2. The composition of claim 1, wherein the particle is a nanoparticle.

3. The composition of claim 1, further comprising a linker to couple the labeled antibodies with labeled protein M.

4. A method comprising:

(a) combining a solution with a nanoparticle conjugated to a complex, the complex comprising (i) antibodies labeled with a fluorophore, the labeled antibodies having target analyte binding sites; and (ii) protein M labeled with a quencher that is complimentary to the fluorophore of the labeled antibodies, wherein the labeled protein M competes with target analytes for the target analyte binding sites on the labeled antibodies;

wherein the fluorophore and quencher are spectrally matched such that there is a detectable change in the fluorescent signal of the labeled antibodies when the fluorophore and the quencher are moved into or out of proximity to each other, and wherein fluorescent light levels change proportionately in response to the amount of target analytes that are able to bind with the labeled antibodies; and (b) measuring the fluorescence light level related to a presence of the target analytes in the solution.

5. The method of claim 4, wherein the particle is a nanoparticle.

6. The method of claim 4, further comprising a linker to couple the labeled antibodies with the labeled protein M.

7. A method comprising:

introducing particles conjugated to complexes into the living body, the complexes comprising (i) antibodies labeled with a fluorophore, the labeled antibodies having target analyte binding sites; and (ii) protein M labeled with a quencher that is complimentary to the fluorophore of the labeled antibodies, wherein the labeled protein M competes with target analytes for the target analyte binding sites on the labeled antibodies; wherein the fluorophore and quencher are spectrally matched such that there is a detectable change in the fluorescent signal of the labeled antibodies when the fluorophore and the quencher are moved into or out of proximity to each other; wherein fluorescent light levels change proportionately in response to the amount of target analytes that are able to bind with the labeled antibodies; wherein the complexes are configured to bind with one or more target analytes, wherein presence or absence of the one or more target analytes in the living body is correlated with the biological state of the living body;

detecting, by a wearable device mounted on an external surface of the living body, a signal transmitted from the living body, wherein the signal includes an analyte response signal that is related to binding of the one or more target analytes with the complexes; and determining a presence or absence of the one or more target analytes based on the analyte response signal.

8. The method of claim 7, wherein photoexcitation energy is applied by the wearable device.

9. The method of claim 7, wherein the labeled antibodies are further labeled with a nanoparticle.

10. The method of claim 7, further comprising a linker to couple the labeled antibodies with labeled protein M.

* * * * *